US006991907B1

(12) United States Patent
Buechler et al.

(10) Patent No.: US 6,991,907 B1
(45) Date of Patent: Jan. 31, 2006

(54) METHODS FOR THE ASSAY OF TROPONIN I AND T AND COMPLEXES OF TROPONIN I AND T AND SELECTION OF ANTIBODIES FOR USE IN IMMUNOASSAYS

(75) Inventors: Kenneth F. Buechler, San Diego, CA (US); Paul H. McPherson, Encinitas, CA (US)

(73) Assignee: Biosite, Inc., San Diego, CA (US)

( * ) Notice: Subject to any disclaimer, the term of this patent is extended or adjusted under 35 U.S.C. 154(b) by 965 days.

(21) Appl. No.: 09/687,051

(22) Filed: Oct. 12, 2000

Related U.S. Application Data

(63) Continuation of application No. 08/633,248, filed on Apr. 18, 1996, now Pat. No. 6,174,686, which is a continuation-in-part of application No. 08/423,582, filed on Apr. 18, 1995, now Pat. No. 5,795,725.

(51) Int. Cl.
G01N 33/53 (2006.01)
(52) U.S. Cl. .................... 435/7.1; 435/7.92; 435/7.93; 435/7.94; 435/7.95; 435/961; 435/962; 435/971; 435/973; 436/501; 436/517; 436/523; 436/524; 436/528; 436/535; 436/538; 436/546; 436/548; 436/172; 436/811; 436/819
(58) Field of Classification Search ................. 435/7.1, 435/7.2, 7.5, 7.71, 7.72, 7.8, 7.9, 7.92, 7.93–7.95, 435/960, 961, 962, 971, 973; 436/518, 523, 436/528, 535, 538, 811, 819, 501, 517, 524, 436/546, 548, 172
See application file for complete search history.

(56) References Cited

U.S. PATENT DOCUMENTS

| | | | |
|---|---|---|---|
| 4,727,019 A | | 2/1988 | Valkirs et al. |
| 5,141,736 A | * | 8/1992 | Iwasa et al. ............. 530/387.3 |
| 5,458,852 A | | 10/1995 | Buechler et al. |
| 5,480,792 A | * | 1/1996 | Buechler et al. ................ 435/6 |
| 5,756,682 A | * | 5/1998 | Wicks et al. ................ 435/7.92 |

FOREIGN PATENT DOCUMENTS

| | | |
|---|---|---|
| DE | 3922873 | 7/1989 |
| DE | 4243648 | 12/1992 |
| DE | 4405249 | 2/1993 |
| GB | 2248688 | 4/1992 |
| GB | 2275774 | 9/1994 |
| WO | 9413774 | 6/1994 |
| WO | 9427156 | 11/1994 |

OTHER PUBLICATIONS

Adams, et al., "Comparable Detection of Acute Myocardial Infarction by Creatine Kinase MB Isoenzyme and Cardiac Troponin I," *Clin. Chem.* 40:1291-1295 (1994).
Ball, et al., "Isoform Specific Interactions of Troponin I and Troponin C Determines pH Sensitivity of Myofibrillar Ca2+ Activation," *Biochem.* 33:8464-8471 (1994).
Bhavsar, et al., "Development expression of troponin I isoforms in fetal human heart," *FEBS Letters* 292:5-8 (1991).
Bhayana, et al., "Discordance Between Results for Serum Troponin T and Troponin I in Renal Disease," *Clin. Chem.* 41:312-317 (1995).
Blechner, et al., "4Ca2+ Troponin C Forms Dimers in Solutions at Neutral pH that Dissociate upon Binding Various Peptides: Small-Angle X-ray Scatterin Studies of Peptide-Induced Structural Changes," *Biochem.* 31:11326-11334 (1992).
Bodor, et al., "Development of Monoclonal Antibodies for an Assay of Cardiac Troponin-I and Peliminary Results in Suspected Cases of Myocardial Infarction," *Clin. Chem.* 38:2203-2214 (1992).
Burtnick, et al., "The isolation and characterization of the tropomyosin binding component (TN-T) of bovine cardiac troponin," *Can. J. Biochem.* 54:546-553 (1976).
Byers, et al., "Hydrodynamic Properties of Bovine Cardiac Troponin-I and Troponin-T*," *J. Biol. Chem.* 258:2951-2954 (1983).
Collins, et al., "Early Diagnosis of Acute Myocardial Infarction with Use of a Rapid Immunochemical Assay of Creatine Kinase MB Isoenzyme," *Clin. Chem.* 39:1725-1728 (1993).
Cummins, et al., "Cardiac Specific Troponin-I Radioimmunoassay in the Diagnosis of Acute Myocardial Infarction," *American Heart Journal* 113:1333-1344 (1987).
Horwitz et al., "Interaction of Troponin Subunits," *J. Biol. Chem.* 254:350-355 (1979).
Huse, et al., "Application of a Filamentous Phage pVIII Fusion Protein System Suitable for Efficient Production, Screening and Mutagenesis of F9ab) Antibody Fragments," *J. Immunol.* 149:3914-3920 (1992).
Katus, et al., "Diagnostic Efficency of Troponin T Measurements in Acute Myocardial Infaction," *Circulation* 83:902-912 (1991).
Katus, et al., "Intracellular Compartmentation of Cardiac Troponin T and Its Release Kinetics in Patients with Reperfused and Nonreperfused Myocardial Infarction," *Am. J. Cardiol.* 67:1360-1367 (1991).
LaRue, et al., "New Monoclonal Antibodies as Probes for Human Cardiac Troponin I: Epitopic Analysis with Synthetic Peptides," *Molecular Immunology* 29:271-278 (1992).

(Continued)

*Primary Examiner*—Long V. Le
*Assistant Examiner*—Gailene R. Gabel
(74) *Attorney, Agent, or Firm*—Foley & Lardner LLP

(57) ABSTRACT

Antibodies and methods are described for the detection and quantitation of cardiac specific troponin I in samples. Cardiac-specific troponin isoforms exist in various forms in the blood, including free and complexed forms. By selecting antibodies that are insensitive and/or sensitive to these various forms, the present invention can provide immunoassays that more accurately reflect the clinical state of an individual. These described antibodies and methods can be used for providing indicators of myocardial infarction and other cardiac pathologies.

21 Claims, 10 Drawing Sheets

OTHER PUBLICATIONS

Leavis, et al., "Calcium Binding to Cardiac Troponin C 1,2," *Arch. Biochem. Biophys.* 186:411-415 (1978).

Liao, et al., "Coupling of Calcium to the Interaction of Troponin I with Troponin C from Cardiac Muscle," *Biochem.* 33:12729-12734 (1994).

MacGeoch, et al., "The human cardiac troponin I locus: assignment to chromosome 19p13.2-19q13.2," *Hum. Genet.* 88:101-104 (1994).

Metzger, et al., "Skeletal troponin C reduces contractile sensitivity to acidosis in cardiac myocytes from transgenic mice," *Proc. Natl. Aca. Sci. USA* 90:9036-9040 (1993).

Olah, et al., "A Model Structure of the Muscle Protein Complex 4Ca2+ TroponinC Troponin I Derived From Small-Angle Scattering Data: Implications for Regulation," *Biochem.* 33:12800-12806 (1994).

Olah, et al., "Troponin I Encompasses and Extended Troponin C in the Ca2+- Bound Complex: A Small- Angle X-ray and Neutron Scattering Study," *Biochem.* 33:8233-8239 (1994).

Pearlstone, et al., "Effects of Troponin-I Plus-C on the Binding of Troponin-T and its Fragments to Tropomyosin," *J. Biol. Chem.* 258:2534-2542 (1983).

Pearlstone, et al., "The interaction of rabbit skeletal muscle troponin -T fragments with troponin-I," *Can. M. Biochem. Cell. Biol.* 63:212-218 (1985).

Pluskal, et al., "Immunobilon PVDF Transfer Membrane: A new Membrane Substrate for Western Blotting of Proteins," *BioTechniques* 4:272-283 (1986).

Potter, "Preparation of Troponin and It's Subunits," *Methods in Enzymology* 85:241-263 (1982).

Sai-Ming Ngai, et al., "Biologically Important Interactions between Synthetic Peptides of the N-Terminal Region of Troponin I and Troponin C*," *J. Biol. Chem.* 267:15615-15723 (1992).

Schreier, et al., "Cloning, Structural Analysis, and Expression of the Human Slow Twitch Skeletal Muscle/Cardiac Troponin C Gene*," *J. Biol. Chem.* 265:21247-21253 (1990).

Stull, et al., "Phosphorylation of Cardiac Troponin by Cyclic Adenosine 3':5'-Monophosphate-dependent Protein Kinase*," *J. Biol. Chem.* 252:851-857 (1977).

Townsend, et al., "Human Cardiac Troponin T: Indentification of Fetal Isoforms and Assignment of the TNNT2 Locus to Chromosole lq," *Genomics* 221:311-316 (1994).

Vallins, et al., "Molecular cloning of human cardiac troponin I using Polymerase chain reaction," *FEBS Letters* 270:57-61 (1990).

Wilkinson, et al., "Comparison of amino acid sequence of troponin I from different striated muscles," *Nature* 271:31-35 (1978).

Wu, et al., "Creatine Kinase MB Isoforms in Patients with Skeletal Muscle Injury: Ramifications for Early Detection of Acute Myocardial Infaction," *Clin. Chem.* 38:2396-2400 (1992).

Zabel, et al., "Analysis of Creatine Kinase, CK-MB, Myoglobin, and Troponin T Time-Activity Curves for Early Assessment of Coronary Artery Reperfusion After Intravenous Thrombosis," *Circulation* 87:1542-1550 (1993).

Zot, et al., "Structural Aspects of Troponin-Tropomyosin Regulation of Skeletal Muscle Contraction," *Am. Rev. Biophys. Chem.* 16:535-559 (1987).

* cited by examiner

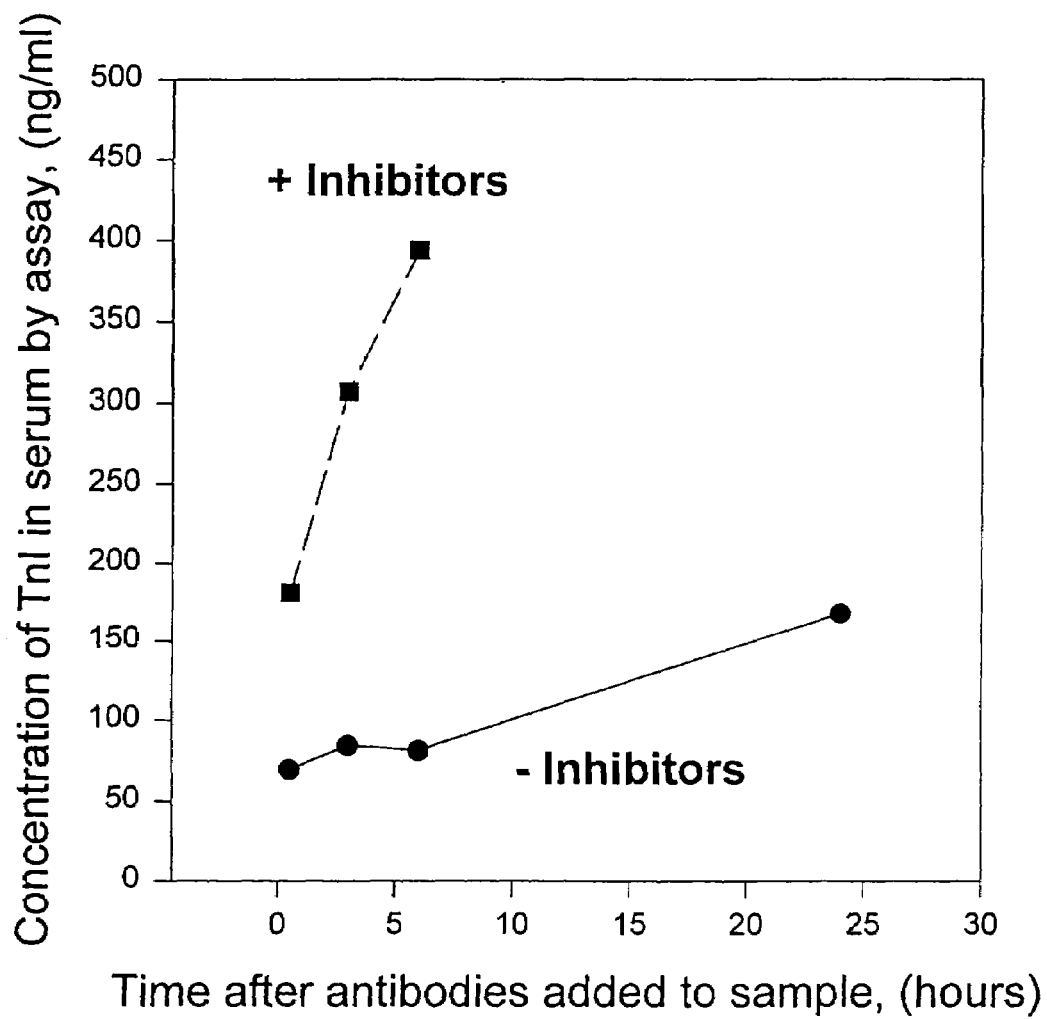

METHODS FOR THE ASSAY OF TROPONIN I AND T AND COMPLEXES OF TROPONIN I AND T AND SELECTION OF ANTIBODIES FOR USE IN IMMUNOASSAYS

CROSS-REFERENCE TO RELATED APPLICATIONS

This application is a continuation of U.S. patent application Ser. No. 08/633,248, filed Apr. 18, 1996, issued as U.S. Pat. No. 6,174,686, which is a continuation-in-part of U.S. patent application Ser. No. 08/423,582, filed 18 Apr. 1995, issued as U.S. Pat. No. 5,795,725, each of which is incorporated by reference herein.

TECHNICAL FIELD

This invention relates to the assay of troponin I and troponin T and complexes of these proteins, and more specifically to the changes in conformation of these proteins in blood, serum and plasma and to the selection of antibodies to the various forms of these proteins and their use in immunoassays. In another aspect of the invention, compositions are taught for the stabilization and recovery of troponin I and T and their complexes in immunoassays.

BACKGROUND ART

Myocardial infarction is one of the leading causes of death in the United States. Approximately 5 million individuals experiencing chest pain are evaluated every year in hospitals throughout the United States, however, less than 30%, of these individuals are subsequently found to have had a myocardial infarction. The accurate and rapid diagnosis of myocardial infarction is important both for the patient suffering a myocardial infarction and for the health care system which can minimize the costs incurred by rapidly identifying individuals who do need treatment.

The diagnosis of myocardial infarction is usually performed in the emergency department of a hospital. An individual having the symptoms of myocardial infarction is treated in different ways depending on the obviousness of the condition. Generally, an electrocardiogram is given to assess the condition of the heart; however, approximately 50% of patients experiencing myocardial infarction have a non-diagnostic electrocardiogram. The physician is then faced with a problem of diagnosing and treating the patient suspected of having a myocardial infarction. Thus, diagnosis and treatment is difficult for patients with a suspected myocardial infarction who have non-diagnostic electrocardiograms.

The World Health Organization (WHO) has instituted guidelines for diagnosing myocardial infarction which state that an individual must exhibit two-of-the-three following criteria: 1) have chest pain or a history of cardiac disease; 2) a diagnostic electrocardiogram; and, 3) elevated creatine kinase (CK) or creatine kinase MB isoenzyme (CKMB). Thus, for the 50% of the individuals who are presented to hospitals for a suspected myocardial infarction and who have a non-diagnostic electrocardiogram, the physician must rely on symptoms of chest pain and an elevated CK or CKMB to diagnose a myocardial infarction.

The assay of CK or CKMB is generally performed in hospital laboratories using sophisticated instrumentation. The assays include enzyme assays and immunoassays which detect the activity or mass of CK or CKMB present in blood samples.

During a myocardial infarction, heart muscle cells die and release their contents to the blood stream. The CKMB is released among such cellular components. CKMB becomes elevated above an otherwise nominal value and can be diagnostic for myocardial infarction. The specificity of CKMB for diagnosing myocardial infarction is not 100% because another source of CKMB in the body is skeletal muscle. Since the mass of skeletal muscle in the body far exceeds the mass of cardiac muscle, through the normal catabolic turnover of skeletal muscle cells, the blood concentration of CKMB in healthy individuals will vary. In general, the concentration of CKMB which may be indicative of myocardial infarction is above 5–7 ng/ml (Circulation 87, 1542–1550 (1993), Clin. Chem. 39, 1725–1728 (1993)). The CKMB concentration of individuals who have skeletal muscle injury or who have exercised has been reported to be elevated above 9 ng/ml (Clin. Chem. 38, 2396–2400 (1992)). Therefore, the problem of specificity when using CKMB as a marker for myocardial infarction has prompted the search for other more specific markers which are released only from damaged heart muscle.

Troponin I and troponin T have recently been shown to be more specific than CKMB for diagnosing myocardial infarction (Circulation 83, 902–912 (1991), Clin. Chem. 40, 1291–1295 (1994). Although troponin T has some disadvantages as a marker because it is elevated in patients experiencing renal disease (Clin. Chem. 41, 312–317 (1995)), the inventive methods herein disclose the successful use of troponin T as a diagnostic marker. The use of troponin I as a diagnostic marker for myocardial infarction also appears to meet many of the clinical requirements (Clin. Chem. 40, 1291–1295 (1994), Clin. Chem. 41, 312–317 (1995)).

The troponin complex in muscle is comprised of troponin I, C and T. These troponin components exist as various tissue specific isoforms. Troponin C exists as two isoforms, one from cardiac and slow-twitch muscle and one from fast-twitch muscle. Troponin I and T are expressed as different isoforms in slow-twitch, fast-twitch and cardiac muscle (Biochem. J. 171, 251–259 (1978), J. Biol. Chem. 265, 21247–21253 (1990), Hum. Genet. 88, 101–104 (1991), Circul. Res. 69, 1226–1233 (1991)). The unique cardiac isoforms of troponin I and T allow them to be distinguished immunologically from the other troponins of skeletal muscle. Therefore, the release into the blood of troponin I and T from damaged heart muscle has been related to cases of unstable angina and myocardial infarction. The prior art, however, has not addressed other forms of troponin I and T in blood.

The troponin complex in muscle is tightly bound to the contractile apparatus. Approximately 6% of the troponin T in cardiac tissue exists as an unbound protein in the cytoplasm and it is believed that this pool of troponin T is released from damaged muscle (Am. J. Cardiol. 67, 1360–1367 (1991)).

The conformations of troponin I, T and C change upon binding when forming binary and ternary complexes (Biochemistry 33, 12800–12806 (1994), J. Biol. Chem. 254, 350–355 (1979), Ann. Rev. Biophys. Biophys. Chem. 16, 535–559 (1987)). An understanding of the conformational changes of troponin I and troponin T and the heterogeneity of the proteins in the blood is critical for the development of accurate diagnostic procedures for measuring troponin I and troponin T concentrations. In addition, troponin I is reported to be unstable in blood (Direction Insert for Troponin I Immunoassay, Sanofi/ERIA Diagnostics Pasteur, Marnes la Coquette, France), and the mechanisms responsible for the instability have not been understood. This invention addresses these problems and provides for stable troponin I and T compositions which are useful in immunoassays.

The teachings of the instant invention provide methods for the selection of antibodies and their use in immunoassays for troponin I and troponin T and complexes of these proteins. These proteins, along with troponin C, exist in both cardiac and skeletal muscle mainly as a ternary complex. In the muscle, the troponin complex is bound to tropomyosin which is, in turn, bound to the actin comprising the thin filaments. The state of troponin I and troponin T, whether free or bound as binary or ternary complexes, which are released from the muscle, has not been previously investigated.

DISCLOSURE OF THE INVENTION

Disclosed is an immunoassay system for determining the presence or amount of a troponin form or a group of troponin forms in a whole blood, plasma or serum sample suspected of containing troponin from damaged heart muscle. The system comprises: a) formation of an antibody conjugate comprising an antibody coupled to a signal generating element, said antibody capable of specifically binding to cardiac specific regions of a form of troponin or a group of troponin forms; b) formation of a reaction mixture comprising said whole blood, plasma or serum sample incubated with said antibody conjugate; c) application of said reaction mixture to a surface to which is bound at least one capture antibody capable of specifically binding to cardiac specific regions of a form of troponin or a group of troponin forms in said antibody conjugate, said capture antibody binding said antibody conjugate, whereby the immobilized conjugate produces a detectable signal upon formation of sandwich complexes; and, d) relation of detectable signal to the presence or amount of said troponin form or said group of troponin forms in said sample.

Also disclosed are antibodies that are sensitive and antibodies that are insensitive to the form of troponin. An "antibody" refers to: a monoclonal antibody, a polyclonal antibody, a binding fragment of an antibody, a recombinant antibody, or a receptor protein that specifically binds to a target. As used herein, an insensitive antibody is an antibody that yields an assay response that is less than within about a factor of 2 (i.e., 50% of the base value); and preferably yields an assay response that is within about 20% for each form of troponin, measured relative to assay response for the use of that antibody in an assay for a troponin form or group of troponin forms (the base value). Thus, an insensitive antibody is one that will tend to bind more than one form of troponin.

As used herein, a sensitive antibody in an immunoassay is one that yields an assay response that is greater by at least about a factor of 2 larger (i.e., 200% of the base value) and preferably a factor of 5 larger (i.e., 200% of the base value), for one or a group of forms of troponin (the base value), as compared to the assay response for other forms measured. Thus, a sensitive antibody is one that will tend to bend only a single form of troponin.

As used herein the nine troponin forms are: 1) the cardiac ternary complex; 2) the cardiac troponin binary complex of I (oxidized)/T; 3) the cardiac troponin binary complex of I (reduced)/T; 4) the cardiac troponin binary complex of I (oxidized)/C; 5) the cardiac troponin binary complex of I (reduced)/C; 6) the cardiac troponin binary complex T/C; 7) unbound cardiac troponin I (oxidized); 8) unbound cardiac troponin I (reduced); and, 9) unbound cardiac troponin T.

Disclosed is a stabilized composition of troponin; The stabilized composition can comprise a stabilized composition of troponin I, wherein the troponin I is oxidized, the troponin I can be unbound or the troponin I can be in a complex. The stabilized composition can comprise a stabilized composition of the ternary complex of troponin I, T and C.

Disclosed is a method for improving the recovery of troponin I or T from a surface used in immunoassays, said method comprising: contacting with said surface at least one strongly basic peptide, protein, or polymer with a pI value greater than about 8; the method can further comprise a step of washing unbound peptide, protein or polymer from said membrane. Melittin can be the strongly basic peptide used, protamine can be the strongly basic protein used.

DESCRIPTION OF FIGURES

FIGS. 5a–5f illustrate the effect of binding inhibitors on troponin I immunoassays from patient samples with confirmed myocardial infarction.

MODES FOR CARRYING OUT THE INVENTION

Figure 1A:
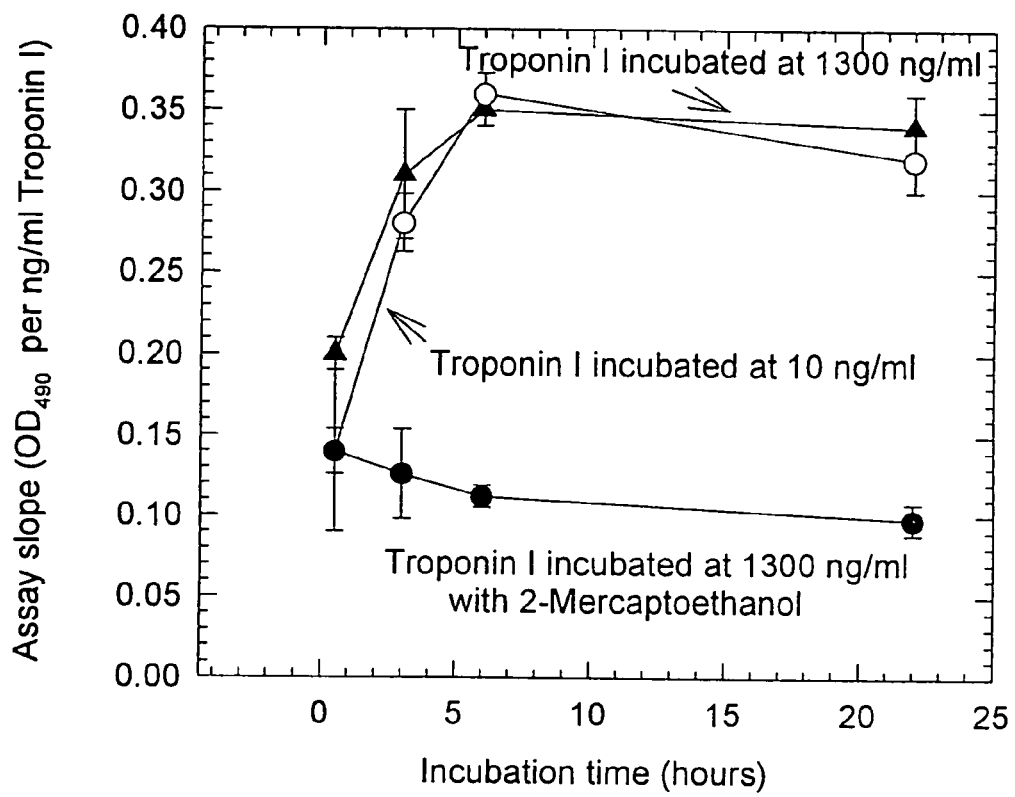
FIG. 1a illustrates the kinetics of air oxidation of troponin I as measured by immunoassay.

Definitions:

As used herein, an "antibody" or "receptor protein" refers to a monoclonal antibody, a polyclonal antibody, a binding fragment of an antibody, a recombinant antibody, or a receptor protein that specifically binds to a target. Specific binding of a substance signifies the quality of that substance that the substance will tend not bind to something to which it does not specifically bind; conversely, the substance will have greater affinity for something it specifically binds that for a something it does not specifically bind.

As used herein, an insensitive antibody in an immunoassay is an antibody that for each form of troponin of interest yields an assay response value that is the same within about a factor of 2, and preferably the same within about 20%, as the assay response values for the other forms of interest. Thus, an insensitive antibody is one that will exhibit a detection of more than one form of troponin in an immunoassay.

As used herein, a sensitive antibody in an immunoassay is one that for one form or group of forms of troponin yields an assay response value that is at least about a factor of 2 larger, and preferably, about a factor of 5 larger, than the assay response values for other forms. Thus, a sensitive antibody is one that will exhibit a preferential detection of one form or group of forms of troponin in an immunoassay.

As used herein the nine troponin forms are: 1) the cardiac ternary complex; 2) the cardiac troponin binary complex of I (oxidized)/T; 3) the cardiac troponin binary complex of I (reduced)/T; 4) the cardiac troponin binary complex of I (oxidized)/C; 5) the cardiac troponin binary complex of I (reduced)/C; 6) the cardiac troponin binary complex T/C; 7) unbound cardiac troponin I (oxidized); 8) unbound cardiac troponin I (reduced); and, 9) unbound cardiac troponin T.

As used herein, a "zone" is a concept that correlates with the ability to identify distinct sensible signals. A zone, therefore, can correspond to a geographic region or correspond to the ability to separately identify distinct sensible signals. The sensible signals can be distinct by, but not limited to, variations between the following characteristics: wavelength of fluorescence or optical absorbance or reflectance; life time of, or transition energy between, electronic states; oxidation-reduction potentials; colorimetric characteristics; or, signal type (e.g., fluorescence vs. radioactivity vs. optical absorbance).

As used herein, unbound troponin is troponin that is not in a complex. A troponin complex can be binary or ternary.

As used herein, a "label", "signal generator" or "signal generating element" is an entity that can embody a number of different forms: Enzymes and their resultant effects on a substrate, colloidal metal particles, latex and silica particles with dye incorporated, and dye particles are examples of signal generators. An enzyme can react on a substrate to produce a product that is sensible, for example, by wavelength of fluorescence (e.g., ultraviolet, visible, infrared), or sensible by affect on pH.

Modes:

This invention is directed to the assay of troponin I and troponin T and complexes of these proteins in body fluids, particularly, in human blood, serum and plasma. The presence of cardiac troponin I and T in the blood, above a nominal concentration, is diagnostic for damaged heart muscle. The teachings of this invention show that troponin I and T exist in various conformations in the blood which may be the same or different than their native conformations in muscle tissue. These various conformations of the troponin molecules can react differently with antibodies.

The ratios of the monomeric troponin I and T and the binary and ternary complexes may be related to the metabolic state of the heart. Based on the reactivities of antibodies to troponin I and T and to purified complexes of the troponins, the concentrations of troponin I and T and their complexes can now be elucidated in blood samples from patients suffering from myocardial infarction.

The embodiments of this invention relate to the conformations of troponin I and T and their complexes in blood, serum and plasma, and to antibodies which recognize those conformations. Specifically, antibodies which recognize troponin I and T in the following forms are preferred: 1) The conformations of troponin I having intramolecularly oxidized and reduced cysteines; 2) The binary complexes of troponin I and T, of troponin I and C, of troponin T and C; and, 3) The ternary complex of troponin I, T and C. In addition, methods are described for the improved recovery of troponin I and T in immunoassays. This invention answers the heretofore unmet need for the assays of troponin I and T in blood.

The focus on troponin I and T for use as markers for myocardial infarction has been based in part on their molecular size: because the proteins are relatively small, it is believed that they leak out of damaged cells faster than the larger proteins.

Antibodies to Troponin Complexes and to Troponin I and T

The term "antibodies or receptor proteins" as used herein refer to monoclonal and polyclonal antibodies, binding fragments of antibodies, and receptor proteins that specifically bend to a target. In a preferred embodiment, receptor proteins, for example, antibodies or binding fragments, are directed to the epitopes of troponin I which are insensitive to the oxidation state of the molecule. The terms sensitive and insensitive herein refer generally to the ability of an antibody to recognize particular forms of free troponin or troponin complexes. In particular, a sensitive antibody which is useful in an immunoassay distinguishes one form or forms of troponin from another form and an insensitive antibody which is useful in an immunoassay does not distinguish one form or forms of troponin from another. The sensitivity or insensitivity of an antibody is exhibited in an immunoassay. To determine whether an antibody is sensitive or insensitive, the antibody is tested with each troponin form independently to yield the assay response of the antibody for each troponin form. In general, a preferred antibody that is insensitive to the troponin form will yield an assay response that is the same, within about a factor of two and preferably within 20%, for each form of troponin. A preferred antibody that is sensitive to the troponin form will yield an assay response that is at least a factor of two, and preferably a factor of five, larger for one form or group of forms as compared with the other form(s). In addition, the terms "troponin I and T" can refer to the free, uncomplexed troponins or to the troponins in the binary or ternary complexes. Human cardiac troponin I contains two cysteines, at positions 80 and 97 (FEBS Letters, 270, 57–61 (1990)). In the current art, during the purification of troponin I from tissues, the oxidation state of troponin I is directed toward the reduced form using various reductants, including mercaptoethanol, dithiothreitol and the like (Can. J. Biochem. 54, 546–553 (1976), Methods Enzymol. 85, 241–263 (1982)). After purification, the current art also teaches to maintain troponin I in the reduced form to prevent intermolecular disulfide formation (J. Biol. Chem. 258, 2951–2954 (1983)).

In the development of immunoassays for a target protein, the purified target protein acts as a standard with which to judge the sensitivity and specificity of the immunoassay using the antibodies that have been selected. As disclosed herein, the cysteines in troponin I can rapidly oxidize, intramolecularly, to alter the conformation of the protein. The degree of oxidation of troponin I has not previously been addressed with respect to its effect on the immunoassay process. The teachings described herein show that an apparent instability in the troponin I molecule is related to the dynamics of the intramolecular oxidation or reduction of the troponin I molecule. In addition, the selection of antibodies is taught for the accurate quantitation of troponin I in blood.

Purified, reduced troponin I undergoes an intramolecular oxidation of the cysteines, the rate of which is not dependent on the troponin I concentration. Special care should be exercised when preparing the oxidized troponin I form, especially in the presence of various thiol reducing agents, because of the possibility of forming mixed disulfides of the protein and the reducing thiol reagent. The mixed disulfide form of the protein may not behave as either the oxidized or reduced form of the molecule, especially if the antibodies used in the immunoassay bind to the region of the protein surrounding cysteines 80 and 97.

Using purified preparations of oxidized and reduced troponin I, differential effects in the immunoassays using various antibodies raised to troponin I were observed. With some antibody pairs, the reduced troponin I was hardly detectable in immunoassays, whereas with other pairs, the oxidation state had no effect on the immunoassay process.

These results showed that selection of antibodies to the troponin I molecule, without prior knowledge of the oxidation state of the troponin I, can result in antibodies and an immunoassay process which gives erroneous results. This conclusion is exemplified by immunoassays of troponin I from patients suffering myocardial infarction. The degree of oxidation of troponin I in patient samples is variable and suggests a possible basis for apparent instabilities of troponin I assays of the current art. The free troponin I does change its oxidation state from the reduced to the oxidized form over time (see Example 4).

In the case when an immunoassay comprising an insensitive antibody is to be utilized to bind to the free and complexed troponin, a preferred antibody is one that is insensitive with respect to the oxidized, reduced and complex forms because the circulating troponin in the blood can change its oxidation state and the degree of binding to other troponin components over time. For example, if reduced, free troponin I is released from the heart, it can transform to the oxidized form during circulation in the blood and until the time troponin is measured. In addition, the free troponin I and T in the blood can bind to each other and to troponin C to form binary and ternary complexes. The outcome of these transformations to the oxidized form of troponin I or to complexes of troponin is that when an antibody is chosen for an immunoassay that is sensitive with respect to the oxidized and reduced forms and complexed forms, the assay will show an apparent increase or decrease in the troponin concentration over time depending on which form (free, oxidized or reduced or complexed) the antibody better recognizes, rather than an actual change in troponin concentration. In another example, the release of troponin complexes from damaged heart muscle can result in the formation of free (uncomplexed) and binary forms of troponin I and T during circulation in the blood or until the troponin is assayed. The variability of assay results of troponin concentrations using immunoassays comprising a sensitive antibody or antibodies can mislead a physician into believing that a patient's condition is improving or deteriorating.

In the case when an immunoassay comprising more than one sensitive antibody is used to measure the free and complexed troponin, each sensitive antibody is intended to be reacted with one form or group of forms of troponin such that the antibody exhibits a maximum assay response for the intended form(s) and a minimum assay response for all other forms. Preferred antibodies are ones for which the assay responses for the intended forms are about the same, preferably within 20%, for all the sensitive antibodies and said minimum assay responses are at least a factor of 2 and preferably a factor of 5 less than the maximum assay responses. For example, if two different antibodies are used for signal antibodies in an immunoassay, and one antibody is insensitive with respect to the oxidized and reduced free troponin I (or the free troponin T) and exhibits a maximum assay response for said free forms of troponin and a minimum assay response for the complexed troponin, then the other antibody should exhibit a maximum assay response for the complexed troponin and a minimum assay response for the free troponin I and T forms. In this way, an accurate measure of total troponin can be determined. One skilled in the art will also recognize that antibodies with different affinities that is, exhibit different assay responses, for the troponin forms can also be utilized in immunoassays when each troponin form is measured alone or in discrete zones and that the relative bias of the immunoassays can be accounted for in the calibration of the assay. Also, sensitive and insensitive antibodies can be attached to solid phases to measure each troponin form in discrete zones.

In another preferred embodiment, antibodies or binding fragments that are directed to the epitopes of the troponin I or T are insensitive with respect to free troponin I or T and troponin complexes. The teachings herein show that antibodies that are sensitive with respect to free troponin I or T and troponin complexes provide methods for the estimation of the extent of binding of troponin I or T in complexes. Using purified preparations of troponin I, T and C, and the purified troponin complexes, the effects of troponin I or T binding in complexes on the recognition of troponin by antibody pairs is taught and is related to the dynamic state of troponin I or T in blood.

The degree of binding of troponin I and T to the components of the troponin complex or to other proteins of the contractile apparatus, including tropomyosin and actin, in blood can also be problematic for immunoassays depending on the degree and affinity of binding. In their native forms, the troponin complex exists in cardiac muscle and in slow- and fast-twitch skeletal muscle as a ternary complex of troponin I, C and T. Troponin I and T from skeletal muscle have different amino acid sequences than troponin I and T from cardiac muscle, respectively; however, troponin C from slow-twitch muscle has the same amino acid sequence as the cardiac muscle protein (Nature 271, 31–35 (1978), Arch. Biochem. Biophys. 186, 411–415 (1978), FEBS Lett. 292, 5–8 (1991)). The fast-twitch skeletal muscle troponin C, although not identical to the cardiac troponin C, can bind to cardiac troponin I (Biochemistry 33, 8464–8471 (1994), Proc. Natl. Acad. Sci. USA 90, 9036–9040 (1993)).

The release of troponin components, that is, troponin I, C and T, or components from the contractile apparatus, for example, tropomyosin and actin, from skeletal muscle, due to the normal turnover of skeletal muscle cells, may result in a significant amount of troponin and contractile apparatus components in the blood. Since skeletal muscle mass is much greater than cardiac muscle mass, the troponin components present in the blood of a normal individual may be derived largely from skeletal muscle. The circulating troponin components which are mainly derived from skeletal muscle would bind to cardiac troponin I and T which are released into the blood during a myocardial infarction or events which lead up to creating damaged heart muscle. As muscle damage progresses in an individual the troponin components derived from heart tissue will presumably rise in the blood. Thus, the concentration of troponin components (bound and free) in the blood from individuals experiencing a myocardial infarction may be differentially derived from both cardiac and skeletal muscle.

The form of troponin released from the heart, whether free or as binary or ternary complexes, into the blood may indicate a particular condition of the heart. The assays taught herein provide for the analysis of release patterns which may allow the physician to diagnose a specific heart failure, for example, unstable angina as compared to myocardial infarction or to determine the time that an infarction occurred.

The clinical impact of an immunoassay measuring only the free troponin I or T from a patient experiencing a myocardial infarction can be very significant. Since the binding of troponin I and T to troponin components in the blood will be variable, depending on the troponin component concentrations, and on the time that has elapsed since the release of the troponin components from muscle an analysis of the bound and free form of the troponin I and T in the blood must be considered. For example, the binding affinity of troponin I to troponin C, in the presence of calcium (which also is present in blood) is $1.27 \times 10^8$ M$^{-1}$ (Biochemistry 33, 12729–12734 (1994)). This implies that if the troponin C concentration is 100 ng/ml and the total (bound and free) troponin I concentration is 8 ng/ml, then the free concentration of troponin I is calculated to be 4.6 ng/ml. If the concentration of troponin I which is indicative of a myocardial infarction is 5 ng/ml or greater, then an assay which measures only the free form of troponin I, in this case, 4.6 ng/ml, will indicate to the physician that a myocardial infarction has not taken place. Generally, in hospital emergency departments which admit patients believed to have had a myocardial infarction, a blood sample from the individual will be obtained again in an hour or two if the first result is negative. In this example, the patient, having a total troponin I concentration of 8 ng/ml in the first sample, (which is defined as positive for a myocardial infarction), but only a measured concentration of 4.6 ng/ml, (which would be defined as a negative result), would not be treated and would continue to accrue damaged heart muscle during the time before a second sample was analyzed. Interpretation of results of troponin T assays would also suffer from troponin T binding to components of the contractile apparatus in blood. Thus, immunoassays of the current art that measure the free troponin I and T may not correctly diagnose a myocardial infarction when the troponin I or T concentration, respectively, is near the decision point. In some cases, the rise or fall of the troponin I or T concentration in a patients blood over time as determined by analyzing blood samples drawn at several different times might be used to diagnose the dynamic condition of the heart, for example, to determine whether the damaged heart is improving with therapy or continuing to deteriorate. In these cases, the time-course of the free troponin I or T concentration could be different than that of the total troponin (bound and free) concentration. One skilled in the art will realize that increasing concentrations of all the troponin components in the blood will result in an increasing fraction of bound troponin I and T relative to free troponin. The concentration of total troponin (bound and free) may rise faster than the concentration of free troponin I and T. An assay that measures the total troponin concentration (bound and free troponin I and T) would be more accurate in assessing progression of heart damage as compared with an assay that measures only free troponin I or T.

In a particularly preferred embodiment, antibodies or binding fragments are directed to the cardiac troponin complex. Specifically, antibodies are directed to cardiac specific epitopes of troponin I and T of the troponin complex or of the troponin I/T, I/C and T/C interfaces in the complex. The teachings herein show that antibodies that are raised to troponin I and T can bind poorly to troponin I or T of the ternary complex. Furthermore, the teachings herein show that the troponin complex exists in the blood of patients who have experienced myocardial infarction. Methods are also described which teach one skilled in the art to assess the amount of troponin complex in the blood relative to the free troponin I and T or binary complexes of troponin I and T, using antibodies which bind to the free troponin molecules.

The equilibrium among the binary and ternary complexes of troponin and free troponin I and T will be altered during the immunoassay process because of the binding of antibodies to the troponin components and complexes. The change in the mole fractions of the various species during the immunoassay may be significant or insignificant and will be a function of the antibody concentrations, the affinity of the antibodies for the troponin components and complexes, the association constants for the troponin components and complexes and the time that the antibodies are allowed to bind to the troponin. These variables can change the perceived concentration of troponin I and T and lead to erroneous conclusions about the troponin concentration. For example, if two immunoassays utilize different antibody pairs for performing a sandwich immunoassay and their antibody concentrations and affinities for troponin I or T are different, and if a proportion of the troponin I or T occurs in the sample as binary and ternary complexes, one may expect that each immunoassay will give a different result. In addition, if blood samples contain varying concentrations of troponin C, then the proportion of troponin I and T that is bound to troponin C as a binary complex will differentially perturb each immunoassay.

The teachings of the instant invention demonstrate that the troponin ternary complex is more stable to dissociation than the binary complexes of troponin.

In another preferred embodiment, antibodies or binding fragments are directed to epitopes which are not changed by proteolytic degradation of the N-terminal region of troponin I. The conformation of troponin I is also reported to be affected by phosphorylation/dephosphorylation (Biophys. J. 63, 986–995(1992), Biochem. 33, 12729–12734 (1994)). In another preferred embodiment, antibodies or binding fragments are directed to epitopes of either troponin I or troponin I complexes, which are or are not changed by the phosphorylation state of troponin I. Troponin I can be phosphorylated using methods described in J. Biol. Chem. 252, 851–857 (1977). The phosphorylated and dephosphorylated preparations of troponin I can be utilized as immunogens for generating antibodies as well as antigens for the selection of antibodies to the phosphorylated and dephosphorylated troponin I. The troponin complex can be dissociated into the component proteins using various treatments, including high concentrations of urea, low pH and metal chelating agents which bind divalent metal cations, particularly calcium and magnesium (Methods Enzymol. 85, 241–263 (1982)). These treatments are, in general, very harsh and require several hours. Thus, these conditions for dissociating the troponin complex are not practical for immunoassays which must be performed in a matter of minutes on samples from individuals who may be suffering a myocardial infarction.

The generation and selection of antibodies that are preferentially either sensitive or insensitive to the binding of troponin I or T in binary complexes are accomplished by first preparing binary troponin I/T, T/C and I/C complexes from purified components (J. Biol. Chem. 254, 350–355 (1979), J. Biol. Chem. 258, 2534–2542 (1983), J. Biol. Chem. 258, 2951–2954 (1983), Can. J. Biochem. Cell Biol. 63, 212–218 (1985), Biochemistry 33, 12729–12734 (1994), Ann. Rev. Biophys. Biophys. Chem. 16, 535–559 (1987)). The complexes may be stabilized, if necessary, by chemically cross-linking the proteins in the complex using methods familiar to those skilled in the art. The generation and selection of antibodies that are sensitive or insensitive to the binding of troponin I or T in the ternary complex can be accomplished several ways. For example, one way is to purify the ternary complex (Methods Enzymol. 85, 241–263 (1983)) or to reconstitute the complex using the purified troponin components. One skilled in the art will recognize that various other contractile apparatus proteins which may be associated with the binary or ternary complexes of troponins can also be constructed from the purified components and that the resultant complex can be utilized to generate and select antibodies as taught by the instant invention. The complex can be stabilized with respect to dissociation by chemically crosslinking the components.

The purified complexes are then injected, for example, into mice or rabbits, to generate polyclonal or monoclonal antibodies. Another way is to purify free (unbound) troponin I or T and then inject the purified free troponin I or T, for example, into mice or rabbits, to generate polyclonal or monoclonal antibodies. One skilled in the art will recognize that many procedures are available for the production of antibodies, for example, as described in *Antibodies, A Laboratory Manual*, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (*Antibody Engineering: A Practical Approach* (Borrebaeck, C., ed.), 1995, Oxford University Press, Oxford; J. Immunol. 149, 3914–3920 (1992)). In particular, the preparation, screening and selection of recombinant binding fragments is described in Examples 22 and 23.

The antibodies which are generated are selected by first screening for affinity and specificity with the purified binary or ternary complexes and comparing the results to the affinity and specificity of the antibodies with the purified troponin I and T molecules for the desired properties which are defined by the immunoassay process.

The screening procedure can involve immobilization of the purified troponin I or T or binary or ternary complexes or peptides to cardiac specific sequences of the troponins in separate wells of microtiter plates. The solution containing a potential antibody or groups of antibodies is then placed into the respective microtiter wells and incubated for about 30 min to 2 h. If an antibody to the protein of interest is present in the solution, it will bind to the immobilized troponin. In screening antibodies for binding to interfaces of binary or ternary complexes of troponin, an antibody is first selected which binds to the binary or ternary complex immobilized in the microtiter well. That antibody is then further screened for its ability to bind to free troponin components; that is, the potential interface antibody should not bind to free troponin I, C or T which is immobilized in microtiter wells. In addition, the interface antibody should never be capable of forming a sandwich assay with binary or ternary complexes and an antibody which is known to bind to a specific troponin component in the complex in the presence of binding inhibitors which are known to disrupt the troponin complex. If this latter condition is met, then the potential interface antibody should also not be capable of forming a sandwich assay with the troponin complex and an antibody to a different troponin component than was used in the previous screen in the presence of binding inhibitors. If this condition is also met, then an interface antibody has been selected for a binary complex. An extra immunoassay must be performed for selecting an interface antibody to a ternary complex; that is, if the previous two conditions are met, then the potential interface antibody should also not be capable of forming a sandwich assay with the troponin complex and an antibody to a different troponin component than was used in the two previous screens. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the troponin is present. The antibodies which are of interest are then further analyzed for affinity and specificity to the cardiac specific molecules and for complementarity in forming sandwich complexes with the antigens. Those skilled in the art will recognize that many approaches can be taken in producing antibodies or binding fragments and screening and selecting for affinity and specificity for the various troponin antigens, but these approaches do not change the scope of the invention.

Assays for Troponin Complexes and Uncomplexed Troponin I and T

A particularly preferred embodiment of this invention is directed to the assay of troponin I and troponin T, particularly immunoassays, wherein the antibodies selected for the assay bind to cardiac specific sequences of the ternary complex, of the binary complexes and of the uncomplexed (free) troponin I or T in order to measure the complexed (bound) and free fractions of troponin I and T, respectively. The cardiac specific sequences of troponin I and T are described in FEBS Lett. 270, 57–61 (1990) and Genomics 21, 311–316 (1994). A synthetic peptide comprised of 14 amino acids which mimics a cardiac specific sequence of troponin I and methods used to prepare antibodies to the peptide are described in an International Patent Application number PCT/US94/05468.

The immunoassay can be formulated with a cocktail of antibodies to bind all the troponin complexes and the free troponin I and T. Alternatively, the immunoassay can be formulated with specific antibodies that recognize epitopes of the troponin I and T in the complexes and also the unbound troponin I and T. In addition, the immunoassay can be formulated with antibodies that bind epitopes at interfaces of the component proteins in the complexes and antibodies that bind the unbound troponin I and T.

A preferred immunoassay for troponin I or T involves conjugation of an antibody or a cocktail of antibodies to a label or a signal generator to form an antibody conjugate(s), which are capable of binding to cardiac specific regions of the troponin complexes of troponin I or T and to unbound troponin I or T. One skilled in the art will recognize that a signal generator has many forms. Enzymes, colloidal metal particles, latex and silica particles with dye incorporated, and dye particles are examples of signal generators. Antibodies can be conjugated to the signal generators in a variety of ways using heterobifunctional reagents as taught in the Pierce Catalog and Handbook, Pierce Chemical Co., Rockford, Ill. and in Uniform Latex Particles by Leigh B. Bangs, Seragen Diagnostics Inc., Indianapolis, Ind. hereby incorporated by reference. Another antibody or cocktail of antibodies is immobilized on a solid phase, for example, a membrane as taught in BioTechniques 4, 272–283 (1986), and the membrane is placed in a device, for example, as described in U.S. Pat. Nos. 4,727,019 and 5,458,852. The immobilized antibody is complementary to the antibody conjugate. The immobilized antibody and conjugate antibodies form sandwich complexes with the troponin I or T complexes and also form sandwich complexes with troponin I or T, respectively. A plasma or serum sample suspected of containing troponin complexes or components from damaged heart muscle is mixed with the antibody conjugate to form a reaction mixture that is allowed to incubate. The reaction mixture is then applied to the aforementioned device. The sample flows through the membrane and the troponin complexes and components, bound to the antibody conjugates, bind to the immobilized antibodies, and excess, unbound, antibody conjugate is washed away with a wash buffer. The signal is developed and read, either visually or instrumentally.

A particularly preferred immunoassay for troponin I involves conjugation of at least two antibodies to a label or a signal generator to form an antibody conjugate. One of the conjugate antibodies is capable of binding to the troponin T component of the troponin ternary complexes and the other antibody is capable of binding to the free and binary troponin I molecules. Another antibody or cocktail of antibodies is immobilized on a solid phase, for example, a membrane, and the membrane is placed in a device, as described previously. The immobilized antibody is complementary with the antibody conjugate antibodies to form sandwich complexes with either troponin I bound to troponin complexes or to the uncomplexed troponin I. A plasma or serum sample suspected of containing troponin complexes or components from damaged heart muscle is mixed with the antibody conjugate to form a reaction mixture which is allowed to incubate. The reaction mixture is then applied to the aforementioned device. The sample flows through the membrane and the troponin complexes and components, bound to the antibody conjugates, bind to the immobilized antibodies and excess, unbound antibody conjugate is washed away with a wash buffer. The signal is developed and read, either visually or instrumentally. In this assay procedure, the antibody conjugate binds to the troponin I in ternary complexes through the troponin T specific antibody and all free and binary troponin I molecules through the troponin I specific antibody. The capture antibody or antibodies on the solid phase bind antibody conjugates that are bound to free troponin I, and to troponin ternary complexes that contain troponin I.

A particularly preferred immunoassay for troponin I (oxidized and reduced) involves conjugation of at least two antibodies to a label or a signal generator to form an antibody conjugate. One of the conjugate antibodies is capable of binding to the oxidized troponin I and the other antibody is capable of binding to the reduced troponin I molecules. Another antibody or cocktail of antibodies is immobilized on a solid phase in up to 2 discrete zones, for example, a membrane, and the membrane is placed in a device, as described previously. The immobilized antibody is complementary with the antibody conjugate antibodies to form sandwich complexes with either oxidized troponin I or reduced troponin I. A plasma or serum sample suspected of containing troponin components from damaged heart muscle is mixed with the antibody conjugate to form a reaction mixture which is allowed to incubate. The reaction mixture is then applied to the aforementioned device. The sample flows through the membrane and the oxidized and reduced troponin I, bound to the antibody conjugates, bind to the immobilized antibodies and excess, unbound antibody conjugate is washed away with a wash buffer. The signal is developed and read, either visually or instrumentally. In this assay procedure, the antibody conjugates bind to the oxidized troponin I through the oxidized troponin I specific antibody and to the reduced troponin I through the reduced troponin I specific antibody. The capture antibody or antibodies on the solid phase only bind antibody conjugates that are bound to oxidized and reduced troponin I. This immunoassay may have application in the estimation of time after an infarction has occurred.

Another particularly preferred immunoassay for troponin I involves conjugation of an antibody or a cocktail of antibodies to a label or a signal generator to form an antibody conjugate. The antibody conjugate binds to either troponin I bound to troponin complexes or to the uncomplexed troponin I. Immobilized on a solid phase, for example, a membrane, in 3 discrete zones, are antibodies or cocktails of antibodies which bind the ternary complex, the binary complexes of troponin I and the free troponin I, and the membrane is placed in a device, as described previously.

For example, a troponin T antibody which binds to the troponin T of the ternary complex is immobilized in one discrete zone, a troponin I antibody which binds to the troponin I binary complexes (troponin I/C and I/T) is immobilized in another discrete zone and a troponin I antibody which binds to only the uncomplexed troponin I is immobilized in yet another discrete zone. The immobilized antibodies are complementary with the antibody conjugate antibodies to form sandwich is complexes with complexed or uncomplexed troponin I, as defined by each discrete zone. Alternatively, immobilized on a solid phase, for example, a membrane, in 2 discrete zones, are antibodies or cocktails of antibodies which bind the troponin I complexes (binary and ternary) and the free troponin I. For example, a troponin T antibody which binds to the troponin T of the ternary complex and a troponin I antibody which binds to the troponin I of the binary complexes are immobilized in one discrete zone and a troponin I antibody which binds to only the uncomplexed troponin I is immobilized in the second discrete zone. The immobilized antibodies are complementary with the antibody conjugate antibodies to form sandwich complexes with complexed or uncomplexed troponin I, as defined by each discrete zone. A further embodiment of this invention utilizes antibodies on the solid phase for detection of troponin I complexes which bind to the interfaces of the binding domains of troponin I/T and I/C. A plasma or serum sample suspected of containing troponin complexes or components from damaged heart muscle is mixed with the antibody conjugate to form a reaction mixture which is allowed to incubate. The reaction mixture is then applied to the aforementioned device. The sample flows through the membrane and the troponin complexes and components, bound to the antibody conjugate(s), bind to the respective immobilized antibodies in the discrete zones and excess, unbound antibody conjugate is washed away with a wash buffer. The signal is developed and read, either visually or instrumentally. In this assay procedure, the antibody conjugate binds to the troponin I and the troponin I binary and ternary complexes through the troponin I specific antibody or antibodies. The capture antibody or antibodies in discrete zones on the solid phase bind the antibody conjugates that are bound to the uncomplexed troponin I or troponin complexes containing troponin I as defined by each discrete zone. This immunoassay allows quantification of the fractions of troponin I, namely, the complexed and the uncomplexed fractions. The inventive teachings described herein show that uncomplexed and complexed troponin exists in plasma and serum samples from patients with confirmed myocardial infarction. The determination of the complexed and uncomplexed troponin I fractions may yield important clinical data relating to the type and extent of muscle damage, for example, from unstable angina or myocardial infarction or to the success of thrombolytic therapy.

Another particularly preferred immunoassay measures the cardiac troponin ternary complex, the cardiac troponin binary complexes (troponin I/T, T/C and I/C) and the free cardiac troponin I and T. This method involves conjugation of antibodies or a cocktail of antibodies to a label or a signal generator to form an antibody conjugate. The antibody conjugates bind to either troponin T and I bound to troponin complexes or to the uncomplexed troponin T and I. Immobilized on a solid phase, for example, a membrane, in 1 discrete zone, are antibodies or cocktails of antibodies which bind the ternary complex, the binary complexes of troponin I and T and the free troponin I and T, and the membrane is placed in a device, as described previously. For example, a troponin I antibody which binds to the troponin of the ternary complex, up to 3 different antibodies, each recognizing the interfaces of the binding domains of troponin I/T, T/C and I/C, a troponin I antibody which binds to the free troponin I and a troponin T antibody which binds to the free troponin T are immobilized in a discrete zone. The immobilized antibodies are complementary with the antibody conjugate antibodies to form sandwich complexes with complexed and uncomplexed troponin T and I. A plasma or serum sample suspected of containing troponin complexes or components from damaged heart muscle is mixed with the antibody conjugate to form a reaction mixture and it is allowed to incubate. The reaction mixture is then applied to the aforementioned device. The sample flows through the membrane and the troponin complexes and components, bound to the antibody conjugate(s), bind to the respective immobilized antibodies in the discrete zone and excess, unbound antibody conjugate is washed away with a wash buffer. The signal is developed and read, either visually or instrumentally. In this assay procedure, the antibody conjugates bind to the free troponin I and T, to the troponin I and T of the binary complexes and the troponin I or T of the ternary complex. The capture antibodies in the discrete zone on the solid phase bind the antibody conjugates which are specific to the free troponin I and T and to the troponin complexes. This immunoassay allows quantification of the ternary troponin complex, the troponin T/C, I/T, I/C and the free troponin I and T. One skilled in the art will recognize that the antibodies specific to the various troponin forms can be conjugated to one or more signal generators to form antibody conjugates and the antibodies previously described for the conjugates can be attached to the solid phase in a discrete zone. The determination of the total troponin concentration may yield a more sensitive immunoassay for damage to the heart muscle that will, in turn, allow a more rapid diagnosis of unstable angina or myocardial infarction and therefore faster administration of thrombolytic therapy.

A particularly preferred immunoassay for troponin T involves conjugation of at least two antibodies to a label or a signal generator to form an antibody conjugate. One of the conjugate antibodies is capable of binding to the troponin I component of the troponin complexes and the other antibody is capable of binding to the free and binary troponin T molecules. Another antibody or cocktail of antibodies is immobilized on a solid phase, for example, a membrane, and the membrane is placed in a device, as described previously. The immobilized antibody is complementary with the antibody conjugate antibodies to form sandwich complexes with either troponin T bound to troponin complexes or to the uncomplexed troponin T. A plasma or serum sample suspected of containing troponin complexes or components from damaged heart muscle is mixed with the antibody conjugate to form a reaction mixture and it is allowed to incubate. The reaction mixture is then applied to the aforementioned device. The sample flows through the membrane and the troponin complexes and components, bound to the antibody conjugates, bind to the immobilized antibodies and excess, unbound antibody conjugate is washed away with a wash buffer. The signal is developed and read, either visually or instrumentally. In this assay procedure, the antibody conjugate binds to the troponin complexes through the troponin I specific antibody and all free and binary troponin T molecules through the troponin T specific antibody. The capture antibody or antibodies on the solid phase bind antibody conjugates that are bound to free troponin T, and to troponin complexes containing troponin T.

Another particularly preferred immunoassay for troponin T involves conjugation of an antibody or a cocktail of antibodies to a label or a signal generator to form an antibody conjugate. The antibody conjugate binds to either troponin T bound to troponin complexes or to the uncomplexed troponin T. Immobilized on a solid phase, for example, a membrane, in 3 discrete zones, are antibodies or cocktails of antibodies which bind the ternary complex, the binary complexes of troponin T and the free troponin T, and the membrane is placed in a device, as described previously. For example, a troponin I antibody which binds to the troponin I of the ternary complex is immobilized in one discrete zone, a troponin T antibody which binds to the troponin T binary complexes (troponin I/T and C/T) is immobilized in another discrete zone and a troponin T antibody which binds to only the uncomplexed troponin T is immobilized in yet another discrete zone. The immobilized antibodies are complementary with the antibody conjugate antibodies to form sandwich complexes with complexed or uncomplexed troponin T, as defined by each discrete zone. Alternatively, immobilized on a solid phase, for example, a membrane, in 2 discrete zones, are antibodies or cocktails of antibodies which bind the troponin T complexes (binary and ternary) and the free troponin T. For example, a troponin I antibody which binds to the troponin I of the ternary complex and a troponin T antibody which binds to the troponin T of the binary complexes are immobilized in one discrete zone and a troponin T antibody which binds to only the uncomplexed troponin T is immobilized in the second discrete zone. The immobilized antibodies are complementary with the antibody conjugate antibodies to form sandwich complexes with complexed or uncomplexed troponin T, as defined by each discrete zone. A further embodiment of this invention utilizes antibodies on the solid phase for detection of troponin T complexes which bind to the interfaces of the binding domains of troponin C/T and I/T. A plasma or serum sample suspected of containing troponin complexes or components from damaged heart muscle is mixed with the antibody conjugate to form a reaction mixture which is allowed to incubate. The reaction mixture is then applied to the aforementioned device. The sample flows through the membrane and the troponin complexes and components, bound to the antibody conjugate(s), bind to the respective immobilized antibodies in the discrete zones and excess, unbound antibody conjugate is washed away with a wash buffer. The signal is developed and read, either visually or instrumentally. In this assay procedure, the antibody conjugate binds to the troponin T and the troponin T binary and ternary complexes through the troponin T specific antibody or antibodies. The capture antibody or antibodies in discrete zones on the solid phase bind the antibody conjugates that are bound to the uncomplexed troponin T or troponin complexes containing troponin T as defined by each discrete zone. This immunoassay allows quantification of the fractions of troponin T, namely, the complexed and the uncomplexed fractions. The inventive teachings described herein show that uncomplexed and complexed troponin exists in plasma and serum samples from patients with confirmed myocardial infarction. The determination of the complexed and uncomplexed troponin T fractions may yield important clinical data relating to the type and extent of muscle damage, for example, from unstable angina or myocardial infarction or to the success of thrombolytic therapy.

Another particularly preferred immunoassay independently measures the cardiac troponin ternary complex, the cardiac troponin binary complexes (troponin I/T, T/C and I/C) and the free cardiac troponin I and T. This method involves conjugation of antibodies or a cocktail of antibodies to a label or a signal generator to form an antibody conjugate. The antibody conjugates bind to either troponin T and I bound to troponin complexes or to the uncomplexed troponin T and I. Immobilized on a solid phase, for example, a membrane, in 6 discrete zones, are antibodies or cocktails of antibodies which bind the ternary complex, the binary complexes of troponin I and T and the free troponin I and T, and the membrane is placed in a device, as described previously. For example, a troponin I antibody which binds to the troponin I of the ternary complex is immobilized in one discrete zone, 3 different antibodies, each recognizing the interfaces of the binding domains of troponin I/T, T/C and I/C, are immobilized in 3 discrete zones, a troponin I antibody which binds to the free troponin I is immobilized in another zone and a troponin T antibody which binds to the free troponin T is immobilized in another zone. The immobilized antibodies are complementary with the antibody conjugate antibodies to form sandwich complexes with complexed and uncomplexed troponin T and I, as defined by each discrete zone. A plasma or serum sample suspected of containing troponin complexes or components from damaged heart muscle is mixed with the antibody conjugate to form a reaction mixture and it is allowed to incubate. The reaction mixture is then applied to the aforementioned device. The sample flows through the membrane and the troponin complexes and components, bound to the antibody conjugate(s), bind to the respective immobilized antibodies in the discrete zones and excess, unbound antibody conjugate is washed away with a wash buffer. The signal is developed and read, either visually or instrumentally. In this assay procedure, the antibody conjugates bind to the free troponin I and T, to the troponin I and T of the binary complexes and the troponin I or T of the ternary complex. The capture antibodies in discrete zones on the solid phase bind the antibody conjugates which are specific to the free troponin I and T and to the troponin complexes. This immunoassay allows quantification of the ternary troponin complex, the troponin T/C, I/T, I/C and the free troponin I and T. The inventive teachings described herein show that uncomplexed and complexed troponin exists in plasma and serum samples from patients with confirmed myocardial infarction. The determinations of the individual troponin ternary complex, the troponin I and T binary complexes and uncomplexed troponin I and T fractions may yield important clinical data relating to the type and extent of muscle damage, for example, from unstable angina or myocardial infarction or to the success of thrombolytic therapy.

Another particularly preferred immunoassay independently measures the cardiac troponin ternary complex, the cardiac troponin binary complexes (troponin I/T, T/C, I/C, oxidized I/T and oxidized I/C) and the free cardiac troponin I (oxidized and reduced) and T. This method involves conjugation of antibodies or a cocktail of antibodies to a label or a signal generator to form an antibody conjugate. The antibody conjugates bind to either troponin T and I bound to troponin complexes or to the uncomplexed troponin T and I. Immobilized on a solid phase, for example, a membrane, in up to 9 discrete zones, are antibodies or cocktails of antibodies which bind the ternary complex, the binary complexes of troponin I and T and the free troponin I and T, and the membrane is placed in a device, as described previously. For example, a troponin I antibody which binds to the troponin I of the ternary complex is immobilized in one discrete zone, 5 different antibodies, each recognizing the interfaces of the binding domains of troponin I/T, T/C, I/C, oxidized I/T and oxidized I/C are immobilized in up to 5 discrete zones, a troponin I antibody which binds to the free troponin I (oxidized and reduced) is immobilized in up to 2 zones and a troponin T antibody which binds to the free troponin T is immobilized in another zone. The immobilized antibodies are complementary with the antibody conjugate antibodies to form sandwich complexes with complexed and uncomplexed troponin T and I, as defined by each discrete zone. A plasma or serum sample suspected of containing troponin complexes or components from damaged heart muscle is mixed with the antibody conjugate to form a reaction mixture and it is allowed to incubate. The reaction mixture is then applied to the aforementioned device. The sample flows through the membrane and the troponin complexes and components, bound to the antibody conjugate(s), bind to the respective immobilized antibodies in the discrete zones and excess, unbound antibody conjugate is washed away with a wash buffer. The signal is developed and read, either visually or instrumentally. In this assay procedure, the antibody conjugates bind to the free troponin I and T, to the troponin I and T of the binary complexes and the troponin I or T of the ternary complex. The capture antibodies in discrete zones on the solid phase bind the antibody conjugates which are specific to the free troponin I and T and to the troponin complexes. This immunoassay allows quantification of the ternary troponin complex, the troponin T/C, I/T, I/C, oxidized I/T and oxidized I/C and the free troponin I (oxidized and reduced) and T. The inventive teachings described herein show that uncomplexed and complexed troponin exists in plasma and serum samples from patients with confirmed myocardial infarction. The determinations of the individual troponin ternary complex, the troponin I and T binary complexes and uncomplexed troponin I and T fractions may yield important clinical data relating to the type and extent of muscle damage, for example, from unstable angina or myocardial infarction or to the success of thrombolytic therapy.

A particularly preferred immunoassay for troponin measures the concentration of two or more forms of troponin, for example of free and complexed troponin I and or T, utilizing antibodies that have varying degrees of recognition for the different forms of troponin. An antibody or cocktail of antibodies are conjugated to a label or signal generator to form an antibody conjugate. The antibody conjugate has the ability to bind to each form of troponin that is to be quantified. A preferred antibody for the conjugate would be an "insensitive" antibody as defined above. Immobilized on a solid phase, for example, a membrane in a device, in discrete zones are antibodies or cocktails of antibodies that are complementary to the antibody conjugate antibody(s). The essential characteristics of the immobilized antibodies are defined in terms of their responses in the assay, and are, therefore, discussed below after the assay is described. The essential features of the assay can be discussed for the case in which two forms of troponin are to be quantified. In the case when two forms, form 1 and 2, of troponin are to be quantified, two discrete zones are utilized. The system is calibrated using two sets of calibrators in a suitable matrix such as blood, plasma or serum. Preferably one set of calibrators contains form 1 of troponin at various concentrations and the other contains form 2 of troponin. Independently, each of the calibrators is mixed with the antibody conjugate to form a reaction mixture which is allowed to incubate. The reaction mixture is then applied to the aforementioned device. The sample flows through the membrane and the troponin, bound to the antibody conjugate(s), binds to the immobilized antibodies in the discrete zones and excess, unbound antibody conjugate is washed away with a wash buffer. The signal on both zones 1 and 2 is developed and measured for each calibrator. The simplest and preferred system would be one in which the assay signal is linear, or can be approximated to be linear, with respect to the troponin concentration. In this case, the calibration procedure would yield four independent assay slopes defined as follows:

$m_{11}$=assay slope determined on zone 1 using form 1 of troponin as the calibrator  (Eqn. 1a)

$m_{12}$=assay slope determined on zone 1 using form 2 of troponin as the calibrator  (Eqn. 1b)

$m_{21}$=assay slope determined on zone 2 using form 1 of troponin as the calibrator  (Eqn. 1c)

$m_{22}$=assay slope determined on zone 2 using form 2 of troponin as the calibrator  (Eqn. 1d)

and two independent assay constants defined as follows:

$c_1$=assay signal on zone 1 corresponding to zero troponin concentration.  (Eqn. 2a)

$c_2$=assay signal on zone 2 corresponding to zero troponin concentration.  (Eqn. 2b)

One skilled in the art will recognize that the slopes and constants shown in Eqns. 1 and 2 could also be determined in a calibration in which the calibrator solutions are comprised of both forms of troponin at various different ratios of concentrations. A blood, plasma or serum sample suspected of containing forms 1 and 2 of troponin is then assayed as described above for the calibrators. The assay yields two signal values: $S_1$ is the signal measured in zone 1 and $S_2$ is the signal measured in zone 2. The two signals are described by two independent linear equations:

$$S_1 = m_{11}[\text{form }1] + m_{12}[\text{form }2] + c_1 \quad \text{(Eqn. 3a)}$$

$$S_2 = m_{21}[\text{form }1] + m_{22}[\text{form }2] + c_2 \quad \text{(Eqn. 3b)}$$

where [form 1] and form [2] are the concentrations of form 1 and 2 of troponin, respectively, in the sample. Equations 3 can be solved using standard techniques of linear algebra to determine values for [form 1] and [form 2] in the sample if:

$$m_{11}m_{22} - m_{12}m_{21} \neq 0 \quad \text{(Eqn. 4)}$$

(see for example, *Mathematical Methods for Physicists*, Acad. Press, NY, N.Y.). Equations 1 and 4 define, therefore, the assay responses that are required for the antibodies in zone 1 and zone 2 to determine the concentrations of form 1 and form 2 of the troponin from the measured signals $S_1$ and $S_2$. In general, the accuracy of the determination of the concentrations of form 1 and form 2 will increase with an increase in the difference shown in Eqn. 4. The value of the difference required to obtain a satisfactory result will depend on the precision of the calibration and the assay, and the accuracy required for the troponin concentration. For most assay systems, a preferred assay is one in which the antibody or cocktail of antibodies in at least one of the zones is sensitive to whether the troponin is form 1 or form 2, where "sensitive" is defined in a previous section. For example, either the ratio $m_{11}/m_{12}$ or the ratio $m_{22}/m_{21}$ or both should be larger than about 2. This procedure for determining the concentrations of two forms of troponin can be extended to more than two forms. If N forms are to be measured, N discrete zones must be used. A calibration must be performed utilizing a minimum of N+1 calibrator solutions comprised of the N forms of troponin. A sample suspected of containing the N forms of troponin is assayed. The assay signal from each of the N zones is measured; the signal $S_i$ from the i'th zone can be expressed as follows:

$$S_i = \sum_{j=1}^{j=N} m_{ij}[\text{form }j] + c_i \quad \text{(Eqn. 5)}$$

where $m_{ij}$ is the assay slope determined on the i'th zone using form j of the troponin as the calibrator and [form j] is the concentration of form j of the troponin in the sample. Eqn 5 defines a set of N linear equations that can be solved to determine the concentrations of all N forms of troponin using standard techniques if the determinant of the matrix comprised of the $m_{ij}$'s is not equal to zero. For most assay systems, a preferred assay is one in which at least N–1 of the zones contain an antibody or cocktail of antibodies that is sensitive to which form the troponin is in, i.e., the ratio $m_{ii}/m_{ij}$, where I≠j, is greater than about 2. Finally, these concepts can be extended to the case in which the assay response is not linear with the troponin concentration. In this case, the signal measured on the i'th of N zones will be given by the relation:

$$S_i = \sum_{j=1}^{j=N} F_{ij} \quad \text{(Eqn. 6)}$$

where $F_{ij}$ is a function of [form j] that describes the dose-response (Signal as a function of [form j]) of form j on zone I and that is determined in a calibration procedure similar to those described above. Equation 6 describes a system of N non-linear equations which may be solved to determine the concentrations of the N forms of troponin using, for example, approximation (computer) methods familiar to those skilled in the art.

In another embodiment of this invention, inhibitors which affect the affinity constants of the association of troponin I complexes or of troponin T complexes are added to the sample prior to or with formation of the reaction mixture so that the free troponin I or troponin T is measured, respectively. The binding inhibitors may disrupt the troponin complexes or they may open up or partially unravel the complex, such that some or all interactions between the troponin components are broken so that epitopes may be more easily assessable to the antibodies for binding. Inhibitors can be selected from the group of compounds which comprise, but is not limited to, metal chelating agents and peptides which compete with troponin I or troponin T for binding to proteins of the contractile apparatus. Metal chelating agents, particularly those which bind to calcium and magnesium, lower the affinity constant, for example, of troponin I and troponin C binding by about a factor of 10 as compared to the affinity in the presence of calcium (Biochemistry 33, 12729–12734 (1994)). Peptides which affect troponin I and troponin T binding to proteins of the contractile apparatus include mastoparan, melittin and peptide sequences which mimic the troponin I and T sequences at their binding domains with the proteins of the contractile apparatus ((Biochemistry 31, 11326–11334 (1992), J. Biol. Chem. 267, 15715–15723(1992), Biochemistry 33, 8233–8239 (1994)). Other peptides which are useful as inhibitors are those which mimic the binding domains of the troponin components. The binding domains are described, for example, in Ann. Rev. Biophys. Biophys. Chem. 16, 535–559 (1987), and with the binding domain information, one skilled in the art synthesizes the peptide which mimics the peptide of the protein at the binding domain.

In another embodiment of this invention, troponin C is added to the sample prior to or with formation of the reaction mixture of the immunoassay so that all or nearly all of the troponin I or T in the sample will be bound by troponin C during the course of the assay. The troponin C concentration in the sample should be about 0.5 µg/ml to 100 µg/ml and preferably about 1 to 10 µg/ml.

In another embodiment of this invention, troponin C and T are added to samples prior to or with formation of the reaction mixture of immunoassays for troponin I in order to bind all or nearly all of the troponin I in the form of the ternary troponin complex. The troponin C and T concentrations in the sample should be about 0.5 to 100 µg/ml and preferably about 1 to 10 µg/ml.

In yet another embodiment of this invention, troponin C and I are added to samples prior to or with formation of the reaction mixture of immunoassays for troponin T in order bind all or nearly all of the troponin T in the form of the ternary troponin complex. The troponin C and T concentrations in the sample should be about 0.5 to 100 µg/ml and preferably about 1 to 10 µg/ml.

These embodiments wherein troponin components are added to the sample prior to or with formation of the reaction mixture have several advantages.

Firstly, troponin I adsorbs tenaciously to glass surfaces and various membranes which can result in a lower measured troponin I concentration. Troponin T also adsorbs to surfaces. However, when bound to troponin C or in the ternary complex, the adsorptive characteristics of troponin I and T may be dramatically reduced. Thus, the recovery of the troponin I/C or T/C complex or the ternary complex can be better than troponin I or T. In this embodiment, antibodies that recognize the troponin I or T complexes are used in the immunoassays.

Secondly, if antibodies which bind only to the complexed troponin I or T are required, then the antibody selection process is less stringent because the antibodies are not required to have a similar affinity to the free troponin I or T.

One skilled in the art will appreciate the inventive teachings described herein and will recognize with these teachings that addition of reagents to a device or to each other, as recited in the embodiments, has many forms, and these forms are within the scope of this invention.

Stabilization of Troponin I or T for Calibrator Reagents

Troponin I and T are known to be unstable in aqueous formulations, as well as in patient samples. The (apparent) instabilities of the proteins, as taught herein, are related to the oxidation state of the troponin I, the propensity of troponin I and T to form complexes with other troponin proteins and the adsorptive characteristics of troponin I and T onto surfaces.

Stabilization of troponin I is performed by the intramolecular oxidation of the cysteines and the protein is stored without thiol reducing agents, such as mercaptoethanol, dithiothreitol and the like.

The storage of troponin I in solutions containing high concentrations of thiol reductants will maintain the cysteines, overall, in the reduced form. However, intramolecular oxidation and reduction of a protein is a dynamic process whereby the protein will exist for some time in the oxidized form even in the presence of the reductants. In the case of reductants, such as mercaptoethanol or N-acetylcysteine, that is, reductant molecules with only a single thiol group, mixed disulfides of the reductant and the protein thiol will form. The half-life of this mixed disulfide will be a function of the reductant concentration and the rate of intramolecular oxidation; that is, the mixed disulfide can be reduced by both the thiol reductant reagent and the other protein cysteine, assuming that both cysteines are not in the mixed disulfide form. In the case of reducing the intramolecularly oxidized troponin I, the reductant with a single thiol group will reduce the intramolecular cystine to yield a cysteine and a mixed disulfide of the protein. The mixed disulfide of the protein will be reduced by either the cysteine of the protein or the thiol reductant. This process continues and eventually the reductant concentration is depleted to a level where it can no longer maintain the protein in the reduced state. As the reductant concentration approaches the concentration of thiol in the troponin I, the protein cysteine and the thiol reductant reagent can form mixed disulfides, which will not be reduced by the thiol reductant. Alternatively, the protein will oxidize, intramolecularly, and the thiol reductant is not in sufficient concentration to reduce the cystine. The end result, upon depletion of the thiol reductant, will be a mixture of troponin I which is in the intramolecularly oxidized form and protein which is in the mixed disulfide form. Each of these forms of troponin I has a different conformation.

In the case of utilizing thiol reductant reagents which possess two thiol groups, for example dithiothreitol or dithioerythritol, the end result, upon depletion of the thiol reductant, will be only the oxidized form of the troponin I.

Therefore, antibodies which are sensitive to the oxidation state of the troponin I will differentially recognize the various forms of the troponin I in the immunoassay. The immunoassay will then measure an inaccurate concentration of troponin I.

A preferred composition of stabilized troponin I comprises an aqueous solution of the intramolecularly oxidized troponin I. A particularly preferred composition of stabilized troponin I and T comprises a buffered solution of the ternary complex of troponin I, T and C in the presence or absence of calcium and magnesium salts. A preferred range of pH of the solution is between 6 and 9 and a range of calcium and magnesium salts concentrations, for example calcium and magnesium chloride, of between 0.01 mM and 10 mM. A particularly preferred buffered solution consists of up to about 100% human serum or plasma. The ternary complex can be formed from the component troponin I, T and C, or alternatively, it can be isolated and purified from cardiac or skeletal muscle (Methods Enzymol. 85, 241–263 (1982)).

Methods for Improving the Recovery of Troponin I in Membranes

The adsorption of troponin I and T to surfaces and to various proteins is known to occur and this phenomenon can lower the measured troponin concentration. In particular, when immunoassays are performed in devices or instruments which have a large surface area, for example, when membranes or latex particles are incorporated into the assay process, the surface area which is exposed to the sample can lower the recovery of troponin. Membranes made up of nylon or compositions of glass fibers having sizes of between 2 mm×2 mm×1 mm and 40 mm×40 mm×5 mm can influence the recovery of troponin I and T when coupled with the assay process.

The troponin I and T molecules have a high degree of basic amino acids. At physiological pH, the basic amino acids are largely positively charged and these charged groups contribute to the adsorptive behavior of the proteins.

In a preferred embodiment of this invention, various components are added to membranes or latex particles to improve the recovery of troponin I and T in the immunoassay process. Specifically, peptides or proteins which are also strongly basic are added to membranes or latex particles or surfaces of devices involved in the assay process prior to or with addition of the sample or reaction mixture. Preferred compounds for this use include peptides, proteins and polymers with pI values greater than about 8. Included in this group are salmine, lysozyme, cytochromes, protamine, polylysine, polyvinyl amine, melittin and mastoparan. Concentrations of blocking reagents which are added to surfaces or membranes range from about 0.01 mg/ml to 100 mg/ml and typically about 0.1 mg/ml to 10 mg/ml.

EXPERIMENTAL SECTION

Example 1

Preparation of Reagents for Troponin ELISA Immunoassays Preparation of Anti-Troponin Antibody Alkaline Phosphatase Conjugates Alkaline phosphatase (Calzyme, San Luis Obispo, Calif.) in 50 mM potassium phosphate, 10 mM potassium borate, 150 mM sodium chloride, pH 7.0, at 10 mg/ml was derivatized with SMCC (succinimidyl 4-[N-maleimidomethyl] cyclohexane-1-carboxylate, Pierce Chemical Co., Rockford, Ill.) at a 15/1 molar ratio of SMCC/enzyme. The derivatization was performed at room temperature for 90 min and subsequently chromatographed on a GH-25 column (Amicon Corp., Beverly, Mass.) equilibrated in 50 mM potassium phosphate, 10 mM potassium borate, 150 mM sodium chloride, pH 7.0.

The anti-troponin antibodies in 50 mM potassium phosphate, 10 mM potassium borate, 150 mM sodium chloride, pH 7.0, at 10 mg/ml were derivatized with SPDP (N-succinimidyl-3-[2-pyridyldithio]propionate, Pierce Chemical Co.) at a 10/1 molar ratio of SPDP/antibody. The antibody was diluted to 2 mg/ml and Dithiothreitol and taurine were added to the solution at final concentrations of 1 mM and 20 mM, respectively, and the solution was subsequently incubated at room temperature for 30 min. The antibody-SPDP was chromatographed on a GH-25 column (Amicon Corp.) equilibrated in 50 mM potassium phosphate, 10 mM potassium borate, 150 mM sodium chloride, 0.1 mM ethylenediamine tetraacetic acid, pH 7.0.

The SMCC-alkaline phosphatase (in 50 mM potassium phosphate, 10 mM potassium borate, 150 mM sodium chloride, 5 mM magnesium chloride, pH 7.0) and the thiol-antibody (in 50 mM potassium phosphate, 10 mM potassium borate, 150 mM sodium chloride, 0.1 mM ethylenediamine tetraacetic acid pH 7.0), both diluted to 1 mg/ml, were rapidly added to each other with mixing in eqimolar amounts. The solution was incubated at room temperature for 3 hours, after which N-ethyl maleimide was added to a final concentration of 2 mM.

Preparation of Biotinylated Troponin Antibodies

Biotin-XX, succinimidyl ester (6-((6-((biotinoyl)amino) hexanoyl)amino)hexanoic acid, succinimidyl ester, Molecular Probes, Eugene, Oreg.) at 40 mM in dimethylformamide was added slowly with mixing to an antibody solution at 2 mg/ml in 50 mM potassium borate, 150 mM sodium chloride, pH 8.2, (BBS) to achieve a final molar ratio of 20/1 biotin-XX/antibody. The solution was incubated at room temperature for 2 h, after which the solution was dialyzed at 4° C. for at least 12 h.

Preparation of Avidin-HS Magnetic Latex

One ml of Estapor Paramagnetic latex particles (0.94$\mu$, Bangs Laboratories, Carmel, Ind., at 10% solids, washed 4 times with deionized water) in water was added to 9 ml of 0.55 mg/ml avidin-HS (Scripps Laboratories, San Diego, Calif.) in 50 mM Tris hydrochloride, 150 mM sodium chloride, pH 7.5. The latex solution was incubated at 45 C for 2 h. The latex was washed 3 times, each with 10 ml BBS, and resuspended in 10 ml BBS.

Example 2

Immunoassay of Human Cardiac Troponin I and Troponin T

Two immunoassay protocols are described. They were used to detect Troponin I and Troponin T, present in human serum, plasma or in solutions containing purified proteins.

Protocol A

The sample containing troponin I or troponin T was diluted to 1–10 ng/ml troponin I or troponin T in an assay buffer (hereafter called assay buffer) containing 10 mM 3-(N-morpholino) propane sulfonic acid, 650 mM sodium chloride, 1 mM magnesium chloride, 0.1 mM zinc chloride, 1 mg/ml polyvinyl alcohol (10,000 m.w.), 10 mg/ml bovine serum albumin, 1 mg/ml sodium azide, pH 7.0. To 25 $\mu$l of diluted sample in a microtiter plate well was added 50 $\mu$l of assay buffer containing 2.5 $\mu$g/ml anti-troponin I or troponin T antibody conjugates (Example 1) and 2.5 $\mu$g/ml biotinylated anti-troponin I or troponin T polyclonal antibody (Example 1) to form a reaction mixture. After a 30 minute incubation of the reaction mixture at room temperature, 25 $\mu$l of avidin-HS coated magnetic latex (Example 1; 0.5% latex in assay buffer) was added to the microtiter plate well, followed by a 5 minute incubation at room temperature. The magnetic latex was pelleted using a microtiter plate magnet (Perceptive Diagnostics, Cambridge, Mass.) and washed twice in BBS-Tween (20 mM borate, 150 mM sodium chloride, 0.1 mg/ml sodium azide, 0.02% Polyoxyethylene-20-Sorbitan Monolaurate (Tween-20), pH 8.2) and once in TBS (40 mM Tris, 150 mM sodium chloride, pH 7.5) The pellet was resuspended in ELISA amplification reagents (Gibco BRL, Gaithersburg, Md.) according to the manufacturer's instructions. After the amplification was complete, the magnetic latex was pelleted and 80 $\mu$l of the colored supernatant was transferred to a fresh microtiter plate. The absorbance at 490 nm ($OD_{490}$) was measured using a microtiter plate reader (Molecular Devices, Palo Alto, Calif.).

Protocol B

The sample containing troponin I or troponin T was diluted into assay buffer as described in protocol A. To 80 $\mu$l of diluted sample in a microtiter plate well was added 40 $\mu$l of assay buffer also containing 30 $\mu$g/ml anti-troponin I or troponin T monoclonal antibody and 7.5 $\mu$g/ml biotinylated anti-troponin I or troponin T polyclonal antibody (Example 1) that was complimentary to the monoclonal antibody to form the reaction mixture. Aliquots (25 $\mu$l) were removed at various times (2 minutes to 24 hours) and were added to microtiter plate wells containing 25 $\mu$l of avidin-HS coated magnetic latex (0.5% latex solids in assay buffer), followed by a 5 minute incubation. The magnetic latex was pelleted and washed once in BBS-Tween and once in assay buffer. The pellet was resuspended in 25 µl of assay buffer also containing 5 µg/ml of goat anti mouse kappa antibody conjugated to alkaline phosphatase (Southern BioTechnology Associates, Inc., Birmingham, Ala.) followed by a 15 minute incubation. The magnetic latex was pelleted and the remainder of the assay was performed as indicated in Protocol A.

Example 3

Selection of Anti-Troponin I Antibodies that Bind the Oxidized, the Reduced or Both the Oxidized and Reduced Forms of Human Cardiac Troponin I Anti-troponin I antibody conjugates (Example 1) and complimentary biotinylated troponin I polyclonal-antibodies (Example 1) were tested for recognition of intramolecularly oxidized or reduced troponin I. The anti troponin I monoclonal antibodies tested were: clone 2D5 and clone 1A12 (BiosPacific, Emeryville, Calif.), clone 110 and 111 (Research Diagnostics, Inc., Flanders, N.J.) and clone TRI-7 F81 (DAKO Corporation, Carpinteria, Calif.). The biotinylated anti-troponin I antibodies tested were affinity-purified goat polyclonals, specified as peptide 1, peptide 2, peptide 3 or peptide 4 specific (BiosPacific, Emeryville, Calif.). Human cardiac troponin I, (P. Cummins, University of Birmingham, Birmingham, UK) was air oxidized at 1.0 µg/ml as described in example 4 to form the intramolecular disulfide. The oxidized troponin I was diluted to 1–10 ng/ml in assay buffer either without (oxidized sample) or with (reduced sample) dithiothreitol (DTT) at a final concentration of 3 mM, followed by a 3 hour incubation at room temperature to allow reduction of the disulfide by DTT. The oxidized and reduced samples were assayed without further dilution using Protocol A of Example 2. The results are shown in Table 1 and are expressed in terms of a ratio of the assay slope for oxidized troponin I (TnI) divided by the assay slope for reduced troponin I. The assay slope increases with increasing recognition of troponin I by the antibody pair.

The data show that antibodies can be selected that either preferentially bind oxidized or reduced troponin I or bind oxidized and reduced troponin I approximately the same. Selection of the antibodies without regard to the oxidation-reduction state of troponin I can lead to a substantial error in the quantification of the troponin I concentration.

TABLE 1

| Anti troponin I monoclonal antibody | Anti troponin I polyclonal antibody | Ratio of assay slopes (oxized TnI/reduced TnI) |
| --- | --- | --- |
| Clone 2D5 | peptide 1 specific | 8.3 |
| Clone 2D5 | peptide 3 specific | 10 |
| Clone 1A12 | peptide 1 specific | 0.6 |
| Clone 1A12 | peptide 3 specific | 1.3 |
| Clone 1A12 | peptide 4 specific | 1.2 |
| Clone TRI-7 F81 | peptide 1 specific | 0.5 |

TABLE 1-continued

| Anti troponin I monoclonal antibody | Anti troponin I polyclonal antibody | Ratio of assay slopes (oxized TnI/reduced TnI) |
| --- | --- | --- |
| Clone TRI-7 F81 | peptide 2 specific | 0.5 |
| Clone TRI-7 F81 | peptide 3 specific | 0.5 |
| Clone TRI-7 F81 | peptide 4 specific | 0.5 |
| Clone 110 | peptide 4 specific | 0.8 |
| Clone 111 | peptide 3 specific | 1.0 |
| Clone 111 | peptide 4 specific | 0.4 |

Example 4

Oxidation-Reduction of Purified Human Cardiac Troponin I

The kinetics of intramolecular oxidation and reduction of purified troponin I (P. Cummins, University of Birmingham, UK) was measured with an immunoassay (Protocol A, Example 2) using a clone 2D5 antibody conjugate (Example 1) and biotinylated goat anti troponin I peptide 1 polyclonal antibody (Example 1). This antibody pair binds strongly to oxidized troponin I and weakly to reduced troponin I as described in Example 3. The results of the assay are expressed in terms of an assay slope [$OD_{490}$ per ng/ml total (oxidized+reduced) troponin I] in the linear range of the assay. The assay slope increases with the fraction of oxidized troponin I.

Air Oxidation of Reduced Troponin I

The rate of air oxidation of troponin I at two troponin I concentrations was measured. Reduced troponin I at 0.27 mg/ml in a buffer containing 20 mM Tris-HCl, 0.5 M sodium chloride, 60 mM 2-mercaptoethanol, pH 7.5, was diluted to either 1300 ng/ml or 10 ng/ml in assay buffer containing either no or 25 mM 2-mercaptoethanol. The solutions were incubated at room temperature. Aliquots were taken after various incubation times, as indicated in FIG. 1a, diluted to 4 and 8 ng/ml troponin I in assay buffer, and assayed immediately. The results are shown in FIG. 1a, wherein the error bars represent 1 standard deviation (SD).

Peroxide Oxidation of Reduced Troponin I

Figure 1B:
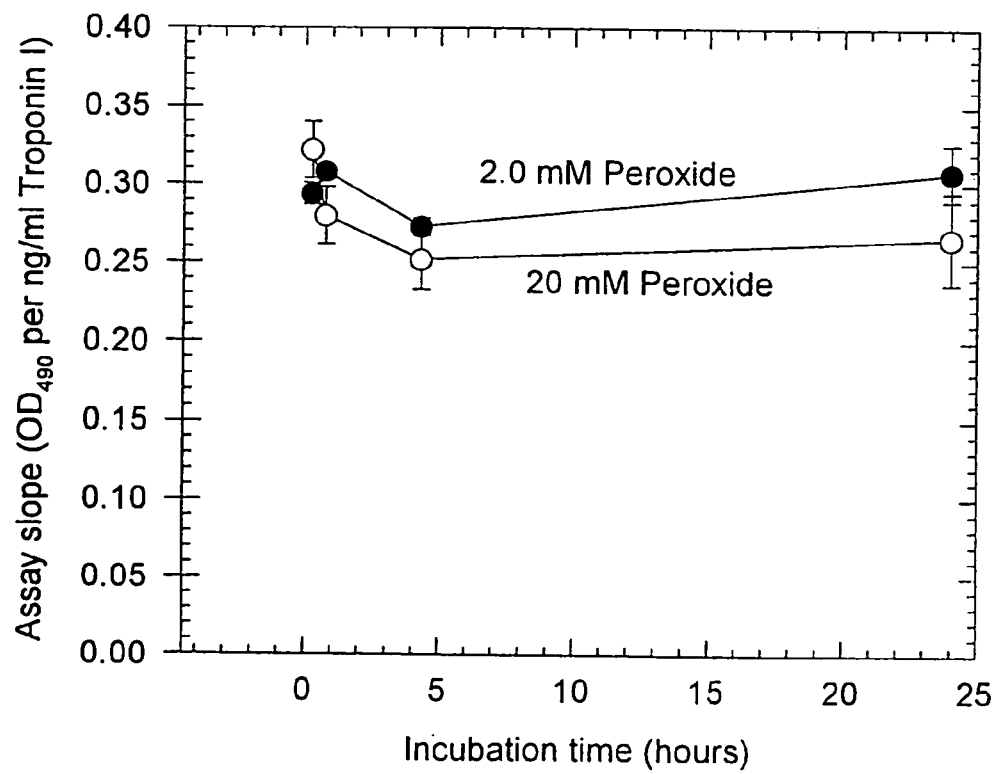
FIG. 1b illustrates the kinetics of oxidation by peroxide of troponin I as measured by immunoassay.

Peroxide (Fisher, unstabilized) was added (final concentration of peroxide 2 mM or 20 mM) to an aliquot of the 1300 ng/ml solution of reduced troponin I (see this example, air oxidation) immediately after the troponin I was diluted from the 0.27 mg/ml stock solution. The solutions were incubated at room temperature. Aliquots were taken after various incubation times, as indicated in FIG. 1b, treated with catalase (Calbiochem, La Jolla, Calif.; 0.01 mg/ml final concentration for 5 minutes) to remove the peroxide, diluted to 4 and 8 ng/ml troponin I, and assayed immediately. The results are shown in FIG. 1b, wherein the error bars represent 1 SD.

DTT Reduction of Oxidized Troponin I

Figure 2:
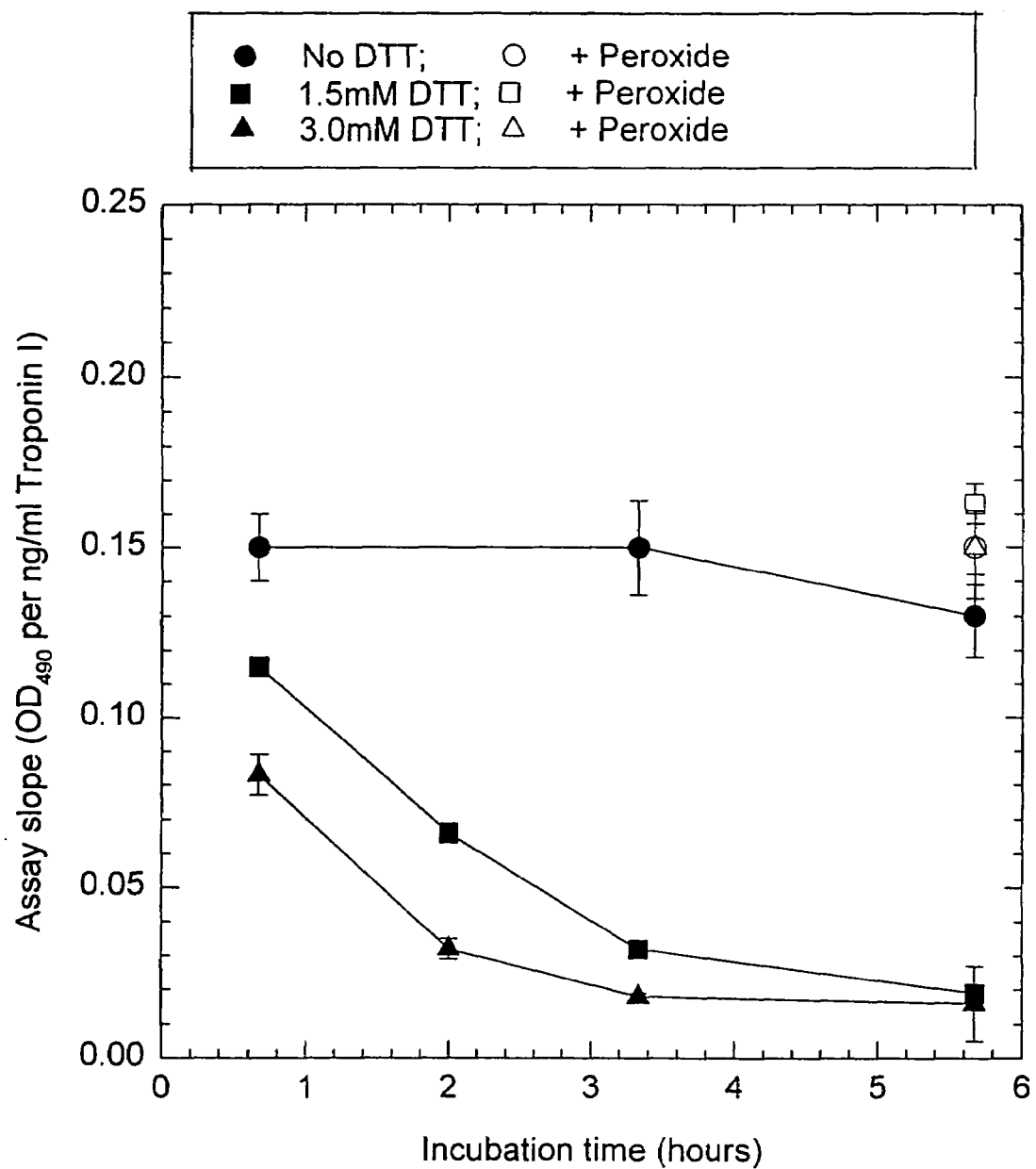
FIG. 2 illustrates the kinetics of reduction by dithiothreitol of troponin I and reoxidation of reduced troponin I by peroxide as measured by immunoassay.

Troponin I that was incubated (air oxidized) at 1000 ng/ml in assay buffer for 15 hours at room temperature was diluted to 4 and 8 ng/ml in assay buffer. DTT was added to a final concentration of 0, 1.5 and 3.0 mM followed by incubation at room temperature for the times indicated in FIG. 2. The aliquots were then assayed for troponin I. After steady state was reached (approximately 6'-hours), aliquots (100 µl) from the three DTT concentration samples were reoxidized with 20 mM peroxide for 15 minutes, treated with catalase for 5 minutes and assayed. The results are shown in FIG. 2, wherein the error bars represent 1 SD.

The data show that the results of an immunoassay can vary over time if the oxidation-reduction state of the troponin I is allowed to change. The oxidation-reduction state of troponin I, and thus the immunoassay results, can be reversibly changed and greatly stabilized over time by the use of oxidants and reductants.

Example 5

Alkylation of Reduced Troponin I

Troponin I was rapidly alkylated using various alkylating reagents. The stock reduced troponin I (University of Birmingham) was at 0.27 mg/ml in 20 mM Tris hydrochloride, 0.5 M sodium chloride, 50 mM 2-mercaptoethanol. Three alkylation reactions (#1–3) were performed and a control was prepared (#4):

1. 20 µl of stock troponin I was added to 20 µl 0.5 M potassium borate, 0.2 mM ethylenediamine tetraacetic acid, pH 8.0 and subsequently, 10 µl 398 mM iodoacetamide was added.
2. 20 µl of stock troponin I was added to 20 µl 0.5 M potassium borate, 0.2 mM ethylenediamine tetraacetic acid, pH 8.0 and subsequently, 10 µl 398 mM iodoacetic acid was added.
3. 20 µl of stock troponin I was added to 20 µl 0.5 M potassium borate, 0.2 mM ethylenediamine tetraacetic acid, pH 8.0 and subsequently, 12.5 µl 319 mM N-ethylmaleimide was added.
4. 20 µl of stock troponin I was added to 20 µl 0.5 M potassium borate, 0.2 mM ethylenediamine tetraacetic acid, pH 8.0 and subsequently, 10 µl 0.5 M potassium borate, 0.2 mM ethylenediamine tetraacetic acid, pH 8.0 was added.

The reactions were incubated at room temperature for 1 h 25 min. During this incubation, the stock troponin I was kept on ice. Aliquots (24 µl) of each solution (1–4) were added to 0.9 µl of 2.9 M mercaptoethanol and were incubated at room temperature for 15 min, after which the samples were frozen in liquid nitrogen. The remaining aliquots of each solution (1–4) were also frozen in liquid nitrogen with no further treatment.

Example 6

Immunoassay of Alkylated Troponin I

Freshly thawed Troponin I alkylated (Example 5) with N-ethyl maleimide (NEM), iodoacetic acid (IHAC), iodoacetamide (IAM), or not alkylated (control sample, Example 5) was diluted to 1–10 ng/ml in assay buffer. A freshly thawed aliquot of the reduced stock troponin I (Example 5) was diluted (standard sample) into assay buffer containing either 0 or 3 mM DTT. Aliquots (25 µl) of all dilutions were taken after either a 0.5 hour or 5.5 hour incubation at room temperature and assayed (Protocol A, Example 2) using a clone 2D5 anti troponin I monoclonal antibody conjugate and biotinylated goat anti troponin I peptide 1 specific polyclonal antibody (Example 1). This antibody pair binds strongly to oxidized troponin I and weakly to reduced troponin I (Examples 3 and 4). Troponin I will remain substantially reduced during a 0.5 hour incubation but will be almost completely oxidized (by air) after a 5.5 hour incubation unless DTT is present to stabilize the reduced form (see Example 4). The results are shown in Table 2 and are given in terms of assay slope ($OD_{490}$ per ng/ml total troponin I) in the linear range. A larger assay slope indicates a stronger binding interaction between the antibodies and the troponin I.

The data show that the antibody pair binds alkylated troponin I similarly to reduced troponin I, that is, weakly in comparison with oxidized troponin I. Furthermore, alkylation stabilizes the immunoassay result with respect to time, similarly to the effect observed by the use of oxidants or reductants to stabilize the oxidation-reduction state of troponin I (Example 4). The lower and more stable assay slope of the control sample as compared with the standard sample is explained by the presence of mixed disulfides formed between the two cysteine residues of the control sample troponin 1 and 2-mercaptoethanol during the room temperature incubation of the control sample at pH 8 (see Example 5).

TABLE 2

| Sample | Assay slope (0.5 hour incubation) | Assay slope (5.5 hour incubation) | Ratio of assay slopes (5.5 hour/0.5 hour) |
| --- | --- | --- | --- |
| reduced TnI standard (+DTT) | 0.030 | 0.030 | 1.0 |
| reduced TnI standard (−DTT) | 0.058 | 0.21 | 3.6 |
| TnI Control | 0.037 | 0.078 | 2.1 |
| TnI alkylated with NEM | 0.023 | 0.026 | 1.1 |
| TnI alkylated with IAM | 0.013 | 0.013 | 1.0 |
| TnI alkylated with IHAC | ≦0.01 | ≦0.01 | |

Example 7

Effect of Peroxide on Immunoassay of Cardiac Troponin I from Patients with Confirmed Myocardial Infarction Frozen Human serum or plasma, drawn in heparin tubes from patients with confirmed myocardial infarction, was obtained from local hospitals. The serum or plasma was thawed at room temperature and immediately split into two aliquots. One aliquot was oxidized at room temperature by the addition of peroxide at a final concentration of 20 mM. The second aliquot was untreated. The oxidation reaction was stopped after 20 minutes by the addition of catalase at a final concentration of 0.01 mg/ml. Ten minutes after the catalase was added both the oxidized and the untreated aliquots were diluted serially by factors of four in assay buffer and assayed immediately for cardiac troponin I using the 2D5 anti troponin I conjugate and biotinylated anti troponin I peptide 3 specific antibodies (Example 2, Protocol A). This complimentary antibody pair binds oxidized troponin I strongly and reduced troponin I weakly (Example 3). Air oxidized (example 4) purified troponin I (P. Cummins, University of Birmingham), diluted to 2, 4, and 8 ng/ml in assay buffer, was assayed with the same antibody reagents to construct a standard curve. The concentration of troponin I in the neat oxidized or untreated serum or plasma sample (Table 3) was calculated from this standard curve using the $OD_{490}$ measurements that fell within the linear range of the assay.

The data show that oxidation of serum or plasma samples from patients with confirmed myocardial infarction can have a substantial effect on the concentration of cardiac troponin I determined by immunoassay. Immunoassay of troponin I in serum or plasma without regard to the oxidation state of the troponin I could lead to a serious underestimation of the troponin I concentration and result in the non-diagnosis of a myocardial infarction.

TABLE 3

| Sample | Time between sample collection and freezing (hours) | Troponin I concentration by assay of untreated sample (ng/ml) | Troponin I concentration by assay of Peroxide oxidized sample (ng/ml) |
| --- | --- | --- | --- |
| 1 Plasma | 2 | 6.3 | 9.4 |
| 2 Plasma | 6.5 | 0.8 | 1.0 |
| 3 Serum | 9.3 | 6.6 | 8.3 |
| 4 Serum | 6.5 | 31.9 | 46.5 |
| 5 Plasma | 6.5 | 31.7 | 49.7 |
| 6 Plasma | 9.5 | 0.6 | 1.0 |
| 7 Serum | 11.5 | 0.4 | 0.4 |
| 8 Plasma | 5.0 | 4.5 | 5.4 |
| 9 Serum | 10.5 | 1.6 | 2.3 |
| 10 Plasma or Serum | unknown | 13.6 | 13.2 |

Example 8

Effect of Peroxide on Immunoassay of Cardiac Troponin I in. Human Plasma after two Freeze/Thaw Cycles.

Plasma sample number 5 (Table 3, Example 7) was stored untreated on ice for three hours after it was initially thawed and then refrozen and stored at −70 C for several days. The plasma was thawed at room temperature and split into two aliquots; one was oxidized with peroxide and the other was left untreated as described in Example 7. The concentration of troponin I in the oxidized and untreated aliquots was determined immediately by the immunoassay described in example 7 and was found to be 53.9 ng/ml in the untreated aliquot and 56.4 ng/ml in the oxidized aliquot.

The data show that oxidation of the plasma after the second thaw did not have a substantial effect on the concentration of cardiac troponin I determined by immunoassay.

Example 9

Immunoassay of Cardiac Troponin I in Oxidized and Reduced Plasma from a Patient with Myocardial Infarction Frozen Human plasma drawn in heparin tubes from a patient with a confirmed myocardial infarction was obtained from a local hospital. The plasma was thawed at room temperature and immediately split into two aliquots. One aliquot was oxidized with peroxide as described in Example 7. The other aliquot was reduced by addition of DTT to a final concentration of 10 mM, followed by a 3 hour incubation at room temperature. The oxidized aliquot was then diluted serially by factors of 2 into assay buffer and the reduced aliquot was diluted serially by factors of 2 into assay buffer containing 3 mM DTT. The diluted aliquots were assayed for troponin I immediately (Protocol A, Example 2) either with the complementary antibody pair clone 2D5 anti troponin I conjugate and biotinylated anti troponin I peptide 3 polyclonal antibody or with the complementary antibody pair clone TRI-7 F81 anti troponin I conjugate and biotinylated anti troponin I peptide 3 polyclonal antibody. Purified troponin I (University of Birmingham) which was air oxidized (example 4) was diluted to 2, 4, and 8 ng/ml in assay buffer and was used to construct the standard curve from which the concentration of troponin I in the neat oxidized or reduced plasma sample was determined. The results are shown in Table 4.

The data show that chemical oxidation and reduction of cardiac troponin I in the plasma sample affects the recognition of the tested antibody pairs for the troponin I in a manner similar to that observed for purified troponin I (Example 3).

TABLE 4

| Monoclonal antibody conjugate | Assayed troponin I concentration (ng/ml) in oxidized plasma | Assayed troponin I concentration (ng/ml) in reduced plasma | Ratio of troponin I concentrations (oxidized plasma/reduced plasma) |
| --- | --- | --- | --- |
| Clone 2D5 | 82 | <1 | >82 |
| Clone TRI-7 F81 | 52.8 | 77.5 | 0.68 |

Example 10

Selection of Anti Troponin I Antibodies that are either Sensitive or Insensitive to the Binding of Troponin C to Troponin I Monoclonal anti troponin I conjugates and complimentary biotinylated anti troponin I polyclonal antibodies (Example 1) were tested for their recognition of free troponin I and troponin I bound to troponin C in a binary complex. Four types of troponin I samples were prepared at room temperature and assayed for troponin I; they are: oxidized troponin I with and without added troponin C and reduced troponin I with and without added troponin C. Oxidized (by air, see Example 4) Human cardiac troponin I (P. Cummins, University of Birmingham) was diluted to 2, 4, and 8 ng/ml in assay buffer containing 2 mM calcium chloride. One aliquot of each concentration of troponin I was either untreated or reduced by the addition of DTT to a final concentration of 3 mM from a 30 mM DTT stock solution in assay buffer to form a reduction reaction. Three hours after the reduction reaction was started, each oxidized and reduced troponin I aliquot was split into two aliquots; to one aliquot was added human cardiac troponin C (Bio-Tech International Inc., Seattle, Wash.) to a final concentration of 0.1 mg/ml from a 1 mg/ml stock solution in 20 mM potassium phosphate, 4 mM potassium borate, 150 mM sodium chloride, pH 7.0 to form a binding reaction mixture, and to the other aliquot was added the same volume of the above buffer without troponin C. One hour after the troponin C was added, all the aliquots were assayed for troponin I (Protocol A, Example 2) using the antibody pairs listed in Table 5. The results in Table 5 are expressed as a fractional assay response which was determined by dividing the assay slope in the presence of troponin C by the assay slope in the absence of troponin C.

The results in Table 5 show that some antibody pairs recognize free troponin I and troponin I bound to troponin C equally well, while other antibody pairs recognize only free troponin I. An immunoassay with antibodies that do not recognize troponin I bound to troponin C will underestimate the total troponin I concentration when some of the troponin I is present as the troponin I/C binary complex.

TABLE 5

| Anti troponin I antibody conjugate | Biotinylated anti troponin I polyclonal antibody | Fractional assay response | |
|---|---|---|---|
| | | Oxidized troponin I | Reduced troponin I |
| Clone 2D5 | Peptide 3 specific | 0.81 | 0.60 |
| Clone 111 | Peptide 1 specific | 0.83 | Not determined |
| Clone 111 | Peptide 3 specific | 0.47 | 0.52 |
| Clone 111 | Peptide 4 specific | 0.59 | 0.19 |
| Clone 110 | Peptide 4 specific | 0.96 | 0.48 |
| Clone 1A12 | Peptide 1 specific | <0.05 | <0.05 |
| Clone 1A12 | Peptide 3 specific | <0.05 | <0.05 |
| Clone 1A12 | Peptide 4 specific | <0.05 | <0.05 |
| Clone TR7 F81 | Peptide 1 specific | 0.74 | 0.79 |
| Clone TR7 F81 | Peptide 2 specific | 0.92 | 1.04 |
| Clone TR7 F81 | Peptide 3 specific | 0.94 | 0.97 |
| Clone TR7 F81 | Peptide 4 specific | 0.70 | 0.79 |

Example 11

Figure 3:
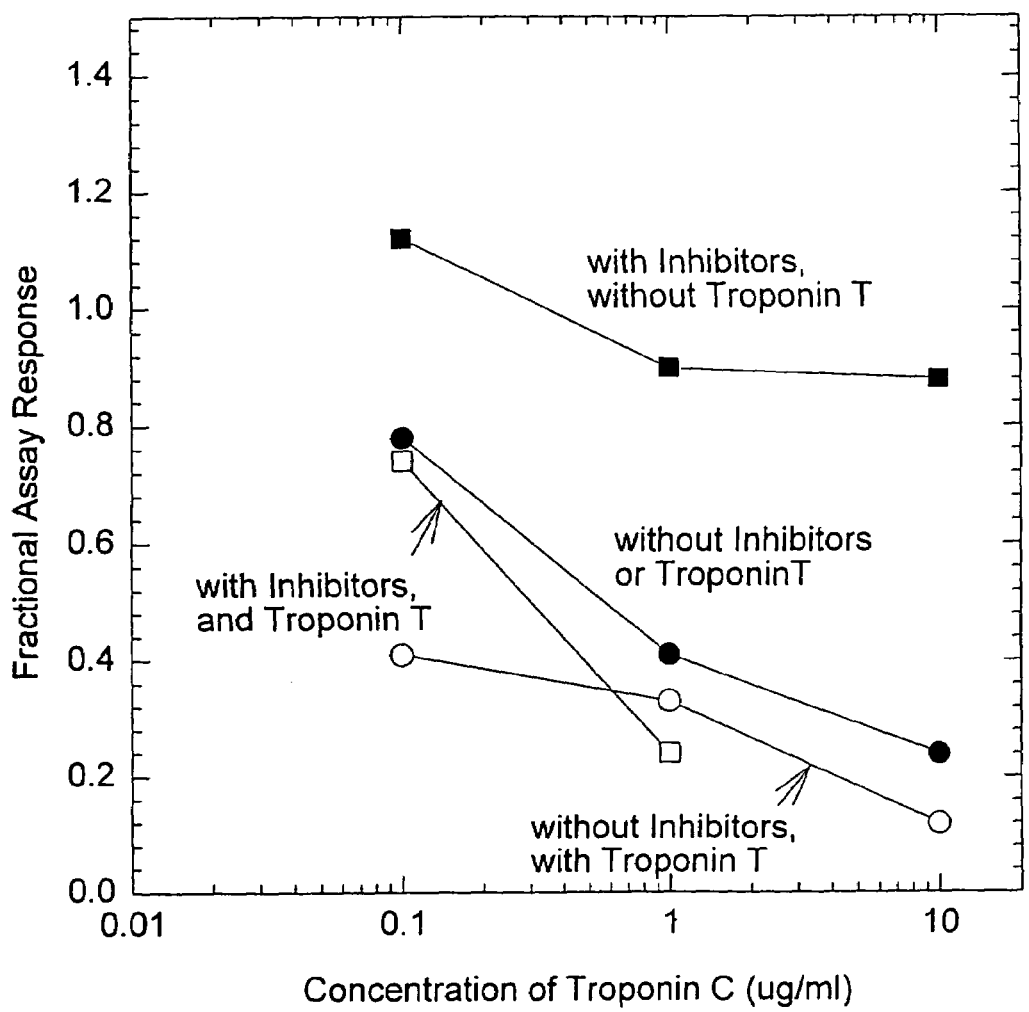
FIG. 3 illustrates the effect of troponin C on the immunoassay of troponin I in the presence or absence of troponin T and binding inhibitors.

Effect of Troponin T. EDTA. Melittin and Mastoparan on a Troponin I Immunoassay with Troponin C Present in large Excess over Troponin I Ethylenediamine tetraacetic acid (EDTA) lowers the binding affinity of troponin I for troponin T and troponin C by chelating calcium and magnesium ions. Melittin lowers the affinity of troponin I for troponin C by binding to troponin C. The effectiveness of EDTA and Melittin (hereafter referred to as binding inhibitors) in breaking up the binary complex of troponin I and troponin C in the presence and absence of troponin T was assessed. Oxidized Human cardiac troponin I (P. Cummins, University of Birmingham) at 1.0 ug/ml in assay buffer containing 2 mM calcium chloride was reduced with dithiothreitol at a final concentration of 3 mM for three hours at room temperature. The reduced troponin I was diluted to 2 and 4 ng/ml in assay buffer containing 2 mM calcium chloride and 3 mM dithiothreitol. Each concentration was split into four aliquots to which were added human cardiac troponin C (Bio-tech International, Inc.) to final concentrations of 0, 0.1, 1.0, and 10.0 µg/ml from 100-fold excess stock solutions in 20 mM potassium phosphate, 4 mM potassium borate, 150 mM sodium chloride, pH 7.0. Each of the resulting aliquots were further split into two aliquots to which was added human troponin T (Scripps Labs) to a final concentration of either 0.0 or 0.1 µg/ml from a 100-fold excess stock solution in deionized water. The aliquots were incubated at room temperature for one hour after the addition of troponin T, then assayed for troponin I (Protocol B, Example 2). The antibody solution added to the microtiter plate wells contained 30 µg/ml clone 1A12 anti troponin 1 and 7.5 µg/ml biotinylated anti troponin I peptide 4 specific antibodies (example 1) either without or with binding inhibitors (30 mM EDTA and 0.15 mM Melittin (Sigma Chemical, Co., St. Louis, Mo.)). Aliquots of the reaction mixtures formed by the addition of antibodies to the troponin I samples were removed after 0.5 h and were further treated as described in Protocol B, Example 2. The assay results for the samples containing no troponin C or T and no binding inhibitors were used to construct a standard dose-response curve. The effect on the standard curve of addition of the binding inhibitors to the assay was tested and found to be negligible. The fractional assay response (shown in FIG. 3) for samples containing inhibitors and troponin components was determined by dividing the assay slope for each sample by the slope of the standard curve.

The data show that in the presence of troponin C, the troponin I concentration is largely underestimated. The binding inhibitors almost completely reverse the effect of troponin C. The presence of troponin T in the absence of troponin C has no effect on the troponin I immunoassay. (Data not shown in FIG. 3). In the presence of troponin C and T, the measured concentration of troponin I is dramatically reduced. The binding inhibitors appear to be less effective at opening up or partially unraveling the troponin complex when the complex is ternary than when the complex is binary. Mastoparan or Melittin at 0.1 mM was also tested as a binding inhibitor to dissociate the I/C complex for a troponin C concentration of 10 ug/ml (Data not shown). The melittin was as effective as the melittin/EDTA (FIG. 3) at increasing the fractional assay response, while the mastoparan was about one third as effective as the melittin at the concentrations tested.

Example 12

Effect of Binding Inhibitors on an Immunoassay of Troponin I in the Presence of Troponin C or Troponin C and T Solutions containing 1.0 µg/ml purified human cardiac troponin I (reduced by DTT, Example 4) and either 1.2 µg/ml human cardiac troponin C (Bio-tech International, Inc.) or 1.2 µg/ml troponin C and 3.1 µg/ml human cardiac troponin T (Scripps Labs) were incubated for 2 hours at room temperature in assay buffer containing 3 mM DTT. Troponin C was added to troponin I prior to addition of troponin T. The troponin solutions were diluted to 2, 4 and 8 ng/ml in terms of troponin I concentration in assay buffer containing 2 mM calcium chloride and 0.5 mM DTT and assayed immediately with and without binding inhibitors as described in example 11. Aliquots of the reaction mixtures of antibodies and troponin components were removed 0.5 h and 2.2 h after the antibodies were added. These aliquots were further treated as described in Protocol B, Example 2. Reduced troponin I without added troponin C and T and without binding inhibitors was assayed to produce a standard curve. The effect on the standard curve of addition of the binding inhibitors to the assay was tested and found to be negligible. The results are expressed in Table 6 as a fraction assay response which was determined by dividing the assay slope for each sample by the slope of the standard curve.

The data show that troponin T and C present in approximately a two fold molar excess above the troponin I concentration substantially lowers the amount of troponin I measured in the immunoassay. Troponin C alone has a smaller effect on the measured troponin I concentration at the antibody concentrations used in this assay. The binding inhibitors partially reverse the effect of troponin C and T at 0.5 h incubation and completely at 2.2 h.

TABLE 6

| Time after antibodies added (hours) | Fractional assay response | | | |
|---|---|---|---|---|
| | With troponin C | | With troponin C and T | |
| | without binding inhibitors | with binding inhibitors | without binding inhibitors | with binding inhibitors |
| 0.5 | 0.88 | 0.94 | 0.55 | 0.75 |
| 2.2 | 1.15 | 1.02 | 0.44 | 1.02 |

Example 13

Assay of Purified Human Cardiac Ternary Troponin Complex for Troponin I

Figure 4:
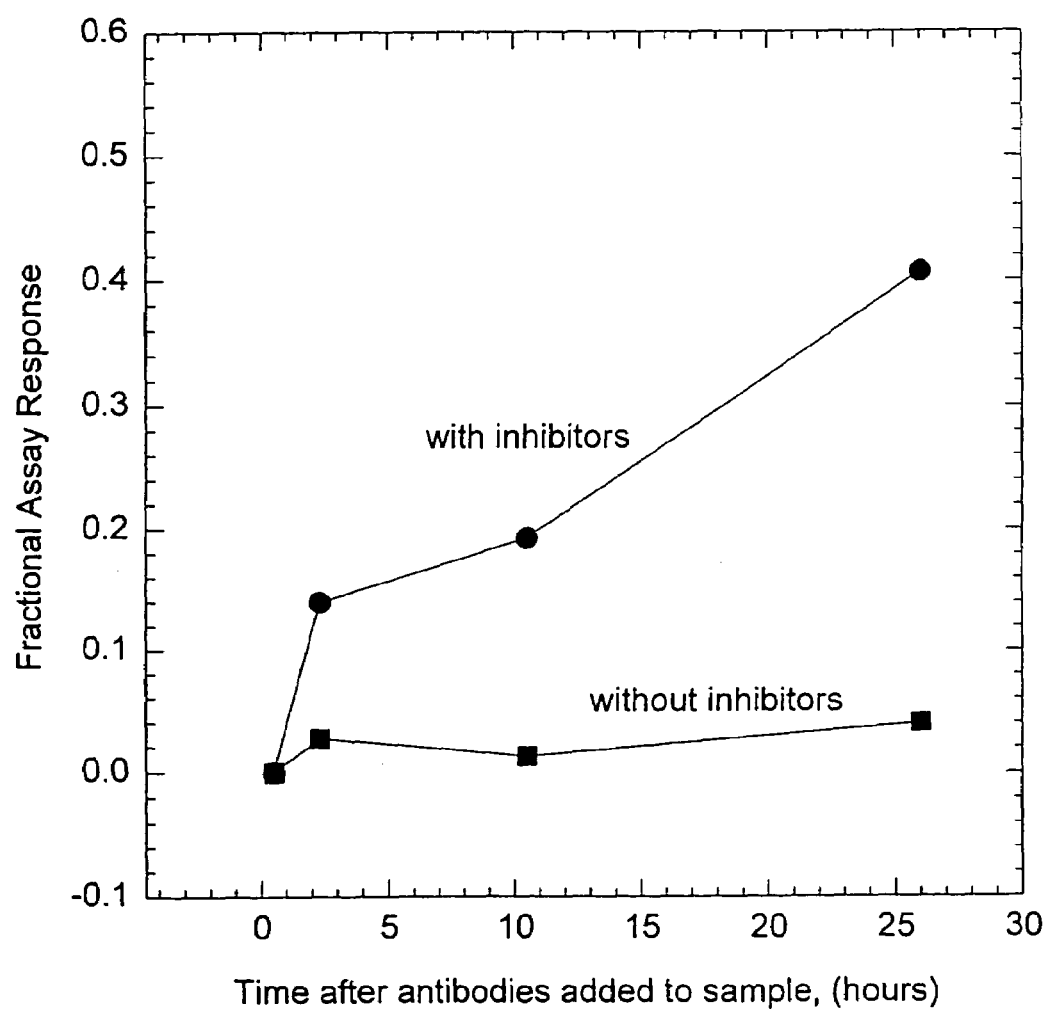
FIG. 4 illustrates the kinetics of disruption of human cardiac troponin ternary complex in the presence or absence of binding inhibitors as measured by an immunoassay for troponin I.
Figure 5A:
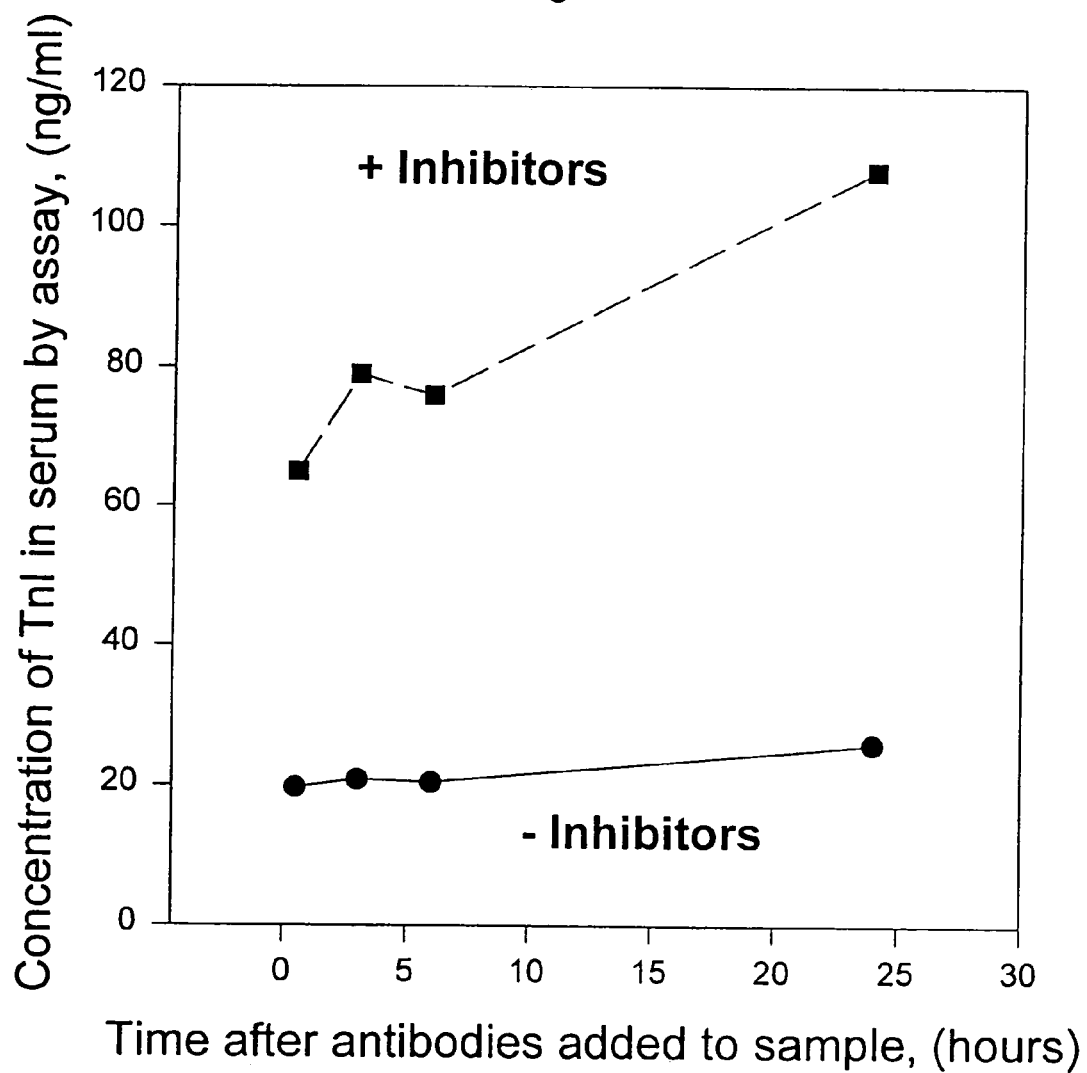
Figure 5B:
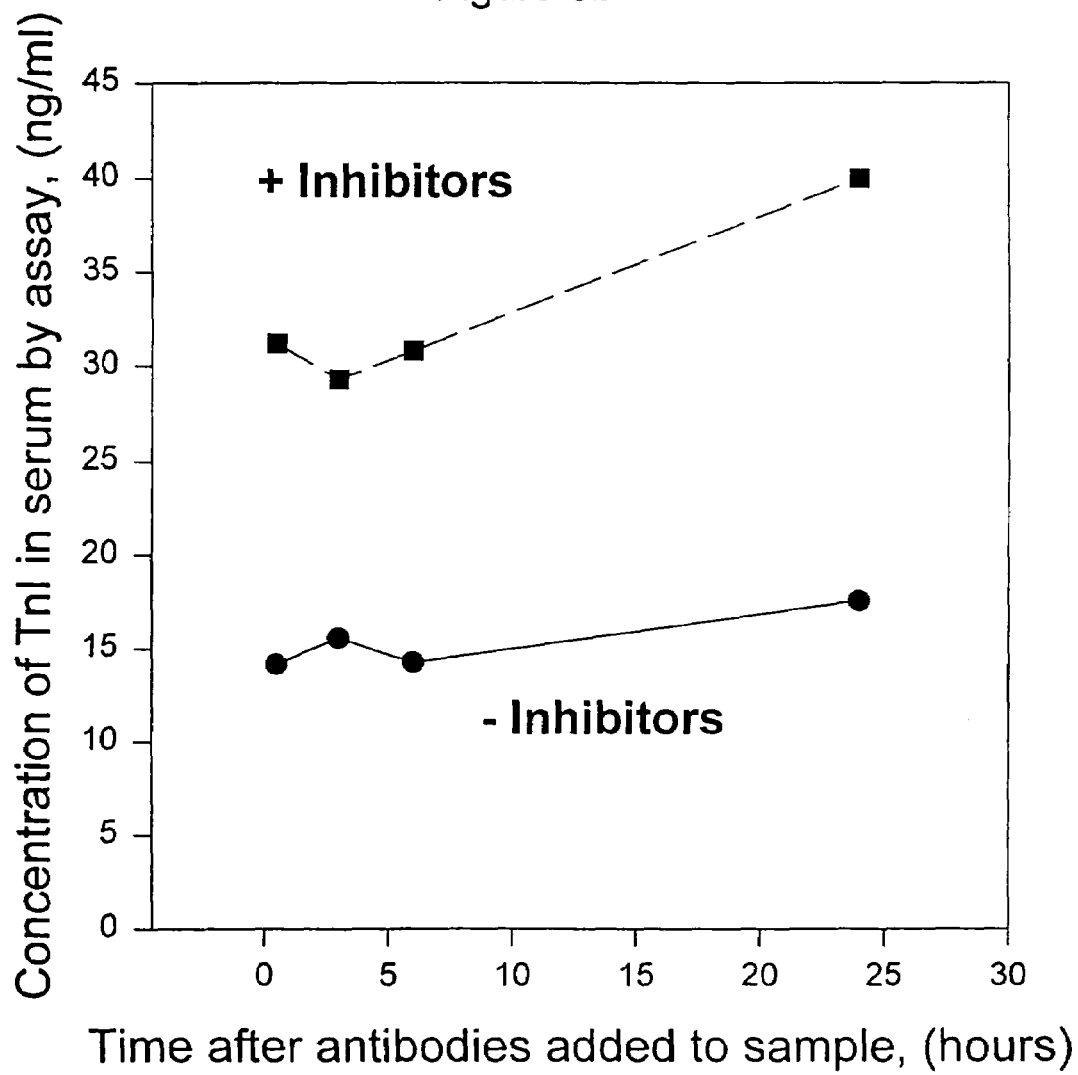
Figure 5D:
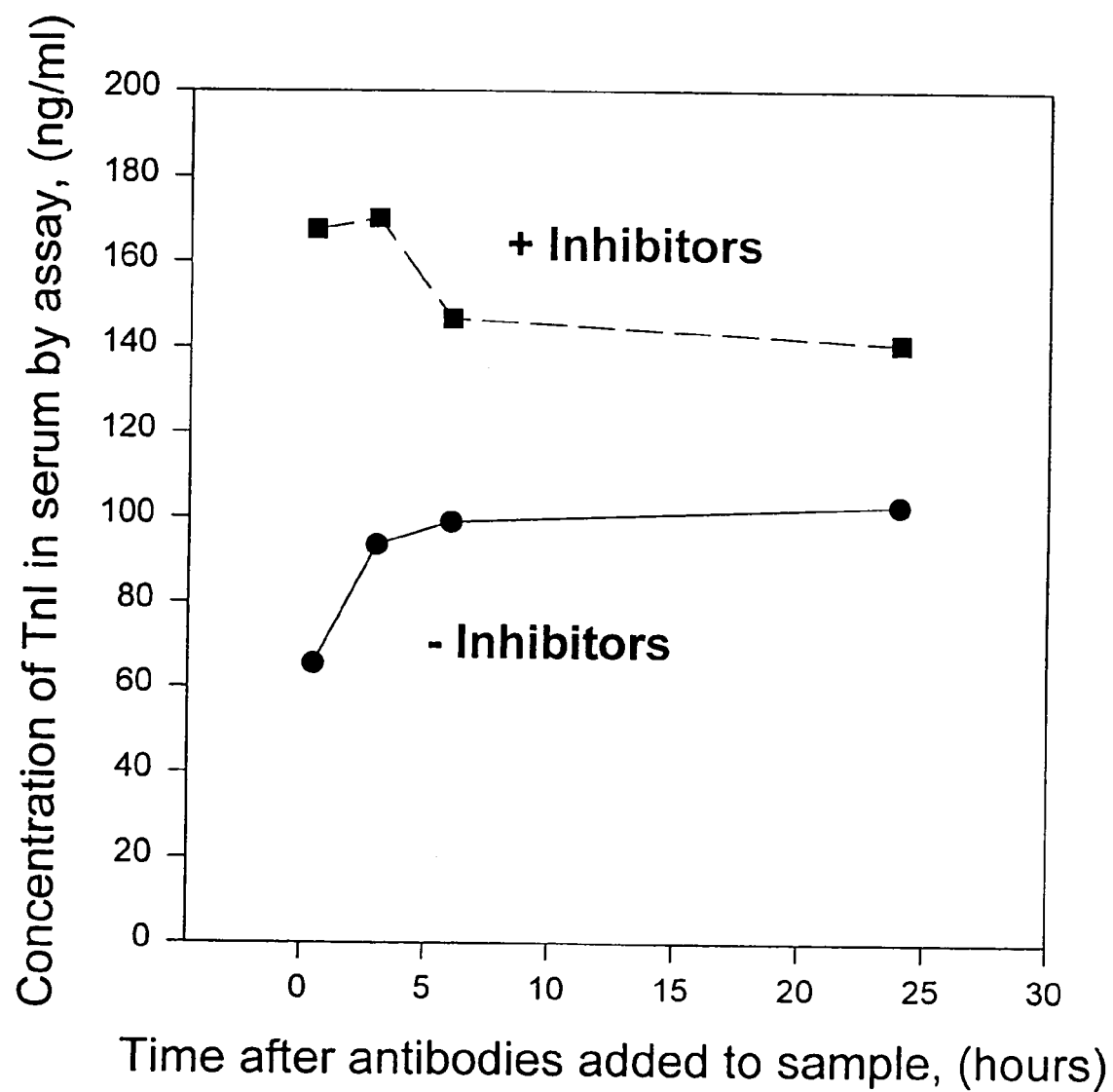
Figure 5E:
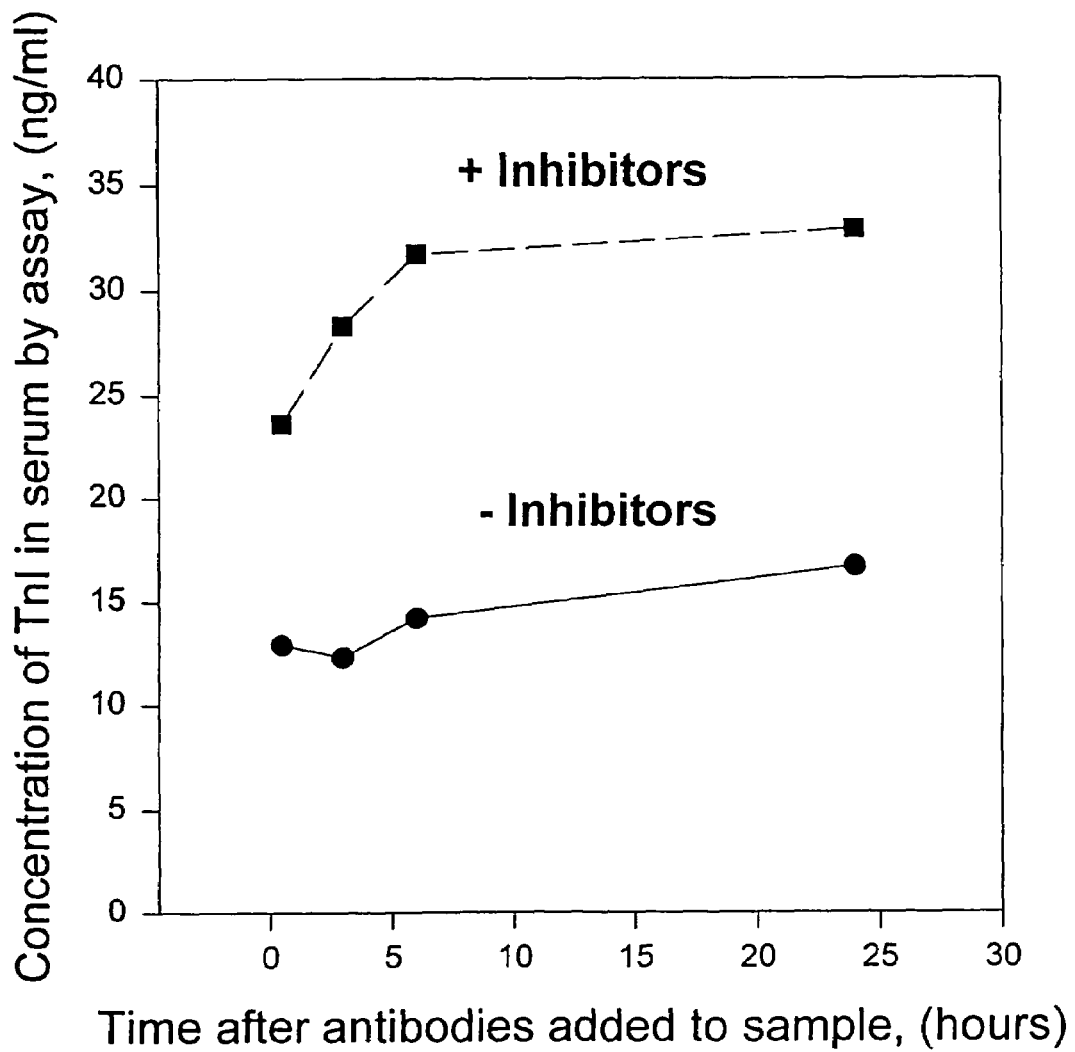
Figure 5F:
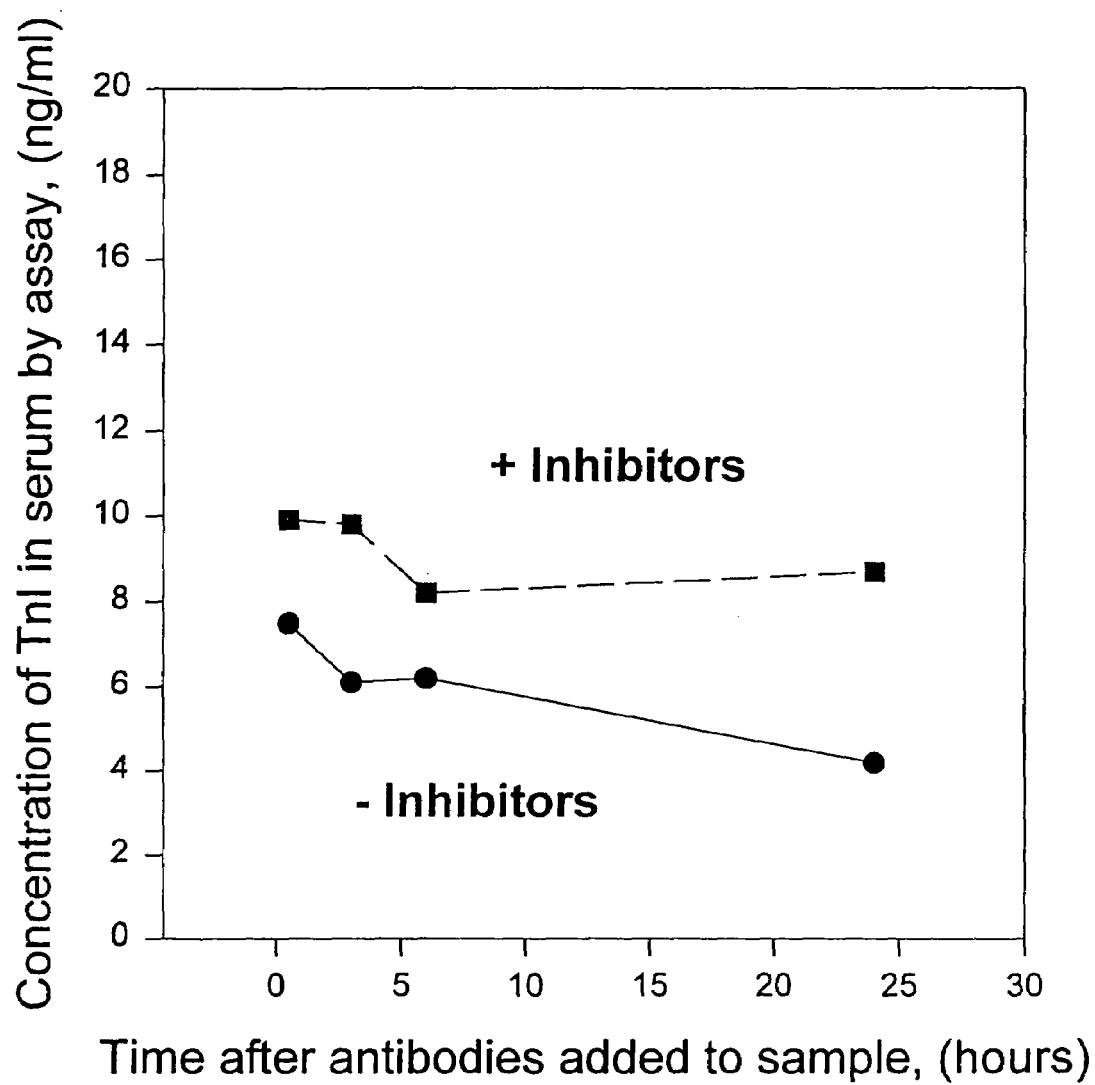

Purified human cardiac ternary troponin complex (Biotech International, Inc., 3 mg/ml stock solution in a buffer containing 20 mM sodium citrate, pH6 was diluted to concentrations ranging from 1 to 15 ng/ml total troponin I in assay buffer containing 2 mM calcium chloride but without the 0.1 mM zinc chloride or the 1 mM magnesium chloride (hereafter called metal-free assay buffer). The diluted solutions were assayed for troponin I with and without binding inhibitors present as described in Example 11. Aliquots of the reaction mixtures of the antibodies with the troponin complex were taken at the times indicated in FIG. 4 and were further treated as described in Protocol B, Example 2. Purified troponin I (Bio-tech International, Inc.) was assayed and used to construct a standard curve. The effect on the standard curve of addition of the binding inhibitors to the assay was tested and found to be negligible. The fractional assay response shown in FIG. 4 was determined by dividing the assay slope for the complex ($OD_{490}$ as a function of total troponin I concentration) by the slope of the standard curve.

The results show that troponin I that is bound in the ternary complex with troponin C and T is not recognized very well by the antibodies at the antibody and troponin I concentrations used in this assay, even after a very long incubation time. In particular, the 30 minute time point had no detectable troponin I, with or without inhibitors. The binding inhibitors slowly open up or partially unravel the complex and thus slowly increase the fraction of troponin I recognized by the antibodies.

Example 14

Effect of Binding Inhibitors on a Troponin I Immunoassay of Plasma and Serum from Patients with Confirmed Myocardial Infarction Frozen serum and plasma drawn in EDTA and Heparin tubes from patients with a confirmed myocardial infarction were obtained from local hospitals and thawed at room temperature. Calcium chloride was added to a final concentration of 6 mM (to bind all the EDTA) and the resultant solution was incubated for two hours at room temperature and then overnight at 4 C. The incubated samples were diluted by factors of two to a maximum dilution factor of 256 in metal-free assay buffer. The diluted samples were immediately assayed for troponin I with and without binding inhibitors as described in Example 11, with the exception that the polyclonal antibody was goat anti-troponin I peptide 3 specific. Aliquots of the reaction mixture formed by the addition of antibodies to the diluted samples were taken at the times indicated in FIGS. 5a–f and further treated as described in Example 2, Protocol B. Oxidized troponin I (University of Birmingham) at 2,4 and 8 ng/ml in metal-free assay buffer was assayed to produce a standard curve. The effect on the standard curve of addition of the binding inhibitors to the assay was tested and found to be negligible. The $OD_{490}$ values measured for the diluted serum or plasma samples were plotted as a function of the inverse of the dilution factor. The slope in the linear region of the resultant curve (typically at $OD_{490} < 2$, which corresponds to a troponin I concentration of less than 8 ng/ml) was divided by the slope of the standard curve to obtain the concentration of troponin I in the neat serum or plasma sample shown in FIGS. 5a–f. Each FIGS. 5a through 5f reflects immunoassays on serum or plasma from different patients.

The data show that the measured concentration of troponin I in all of the serum and plasma samples tested was increased by the addition of binding inhibitors. Importantly, the time profile of the measured concentration of troponin I was in some cases biphasic (FIGS. 5a–c and 5e). The fast phase was complete within the first assay time of 0.5 h. The slow phase continued to rise for 6–24 hours depending on the sample. A slow phase was also observed for the purified ternary troponin complex (Example 13). The slow phase observed for the diluted serum and plasma samples, may, therefore, be associated with the opening up or partial unraveling of a ternary complex by the inhibitors and antibodies. The fast phase indicates a bound complex of troponin I that is more easily opened up or partially unraveled than the ternary complex, since the fast phase is absent for the purified ternary complex (Example 13). Thus, the fast phase could be associated with the opening up or partial unraveling of binary complexes of troponin I.

Example 15

Immunoassays that are Sensitive to Free Troponin I. Troponin I Bound in a Ternary Complex, and Both Free and Bound Troponin I Three sets of antibodies were evaluated for their ability to recognize free troponin I and troponin I bound in the ternary complex. Three antibody stock solutions described is below as #1–3 were prepared in metal-free assay buffer either with or without binding inhibitors (30 mM EDTA and 0.15 mM Melittin) and the following antibodies:

1. 30 µg/ml 1A12 anti troponin 1 and 7.5 µg/ml biotinylated anti troponin I peptide 4 specific;
2. 30 µg/ml 1A12 anti troponin I, 30 µg/ml 9B1 anti troponin T monoclonal (Biospacific), 5 µg/ml each of biotinylated anti troponin I peptide 1, 2, 3 and 4 specific;
3. 30 µg/ml 9B1 anti troponin T and 5 µg/ml each of biotinylated anti troponin I peptide 1, 2, 3 and 4 specific. Human cardiac troponin ternary complex (Bio-tech International, Inc.) was diluted to 1–15 ng/ml troponin I equivalents in metal free assay buffer and purified troponin I (Bio-tech International, Inc.) was diluted to 2,4 and 8 ng/ml in the same buffer. The dilutions of the troponin complex and troponin I were assayed immediately using Protocol B, Example. 2 with antibody solutions #1–3. Aliquots of the reaction mixtures formed by the addition of the antibodies to the troponin complex and troponin I samples were taken at 0.5 h and 2.5 h after the antibodies were added and were further treated as described in Example 2, Protocol B. The results are shown in Table 7 and are expressed in terms of an assay slope with units of $OD_{490}$ per ng/ml total troponin I in the linear range of the assay. A higher slope indicates better binding of the antibodies to the troponin components. Antibody solution #2 was tested and found to be negative for cross reactivity with purified human cardiac troponin T (Scripps Labs) at 1–6 ng/ml using the assay protocol described herein (data not shown).

The data show that the immunoassay using the antibodies in solution #1 recognizes free troponin I but not troponin I in the ternary complex. The immunoassays using the antibodies in solution #2 recognizes free troponin I and troponin I in the ternary complex almost equally well. Thus, antibody solution #2 is superior to solution #1 for the assay of total troponin I when a fraction of the troponin I is present as the ternary complex. The immunoassay using the antibodies in solution #3 recognizes the ternary complex well but recognizes free troponin I poorly. This poor recognition of free troponin I causes the assay slope for antibody solution #3 to decrease over time in the presence of binding inhibitors. By using all three antibody solutions in immunoassays, one can estimate independently the concentrations of free troponin I (solution #1), total troponin I (solution #2) and bound troponin I (solution #3).

TABLE 7

| Antibody solution # | Time after antibodies added (hours) | Free Troponin I | Troponin ternary complex (without binding inhibitors) | Troponin ternary complex (with binding inhibitors) |
|---|---|---|---|---|
| #1 | 0.5 | 0.14 | <0.006 | <0.006 |
| #1 | 2.5 | 0.14 | 0.003 | 0.021 |
| #2 | 0.5 | 0.12 | 0.18 | 0.14 |
| #2 | 2.5 | 0.22 | 0.17 | 0.12 |
| #3 | 0.5 | 0.008 | 0.18 | 0.17 |
| #3 | 2.5 | 0.008 | 0.17 | 0.08 |

Assay Slope ($OD_{490}$ per ng/ml total troponin I)

Example 16

Estimation of Free Troponin I. Bound Troponin I and Total Troponin I in Plasma from a Patient with a Myocardial Infarction The three antibody solutions described in Example 15 were used in immunoassays to measure the troponin I concentration in plasma from a patient with a confirmed myocardial infarction. The frozen plasma was treated and diluted into metal-free assay buffer as described in Example 14. The diluted plasma was assayed for troponin I immediately using Protocol B, Example 2 with antibody solutions #1–3 (Example 15). Aliquots were taken 0.5 h and 2.5 h after the antibodies were added to the samples to form the reaction mixtures and were further treated as described in Example 2, Protocol B. Either free troponin I at 1–4 ng/ml or the troponin complex (Bio-tech International, Inc.) at 1–8 ng/ml troponin I in metal-free assay buffer was assayed and used to construct a standard curve of $OD_{490}$ as a function of total troponin I concentration for each antibody solution. The concentration of troponin I in the neat plasma sample, as shown in Table 8, measured by each antibody solution was determined using either the standard curve for free troponin I or for troponin I in the ternary complex in the absence of binding inhibitors as indicated in Table 8 and as described in Example 14. The ratio determined by dividing the assayed troponin I concentration with binding inhibitors by the concentration without inhibitors is also shown in Table 8.

The data show that the concentration of troponin I determined by immunoassay using antibody solution #1 is much more sensitive to the presence of binding inhibitors and thereby to the opening up or partial unraveling of the troponin complex than that determined using solution #2 or #3. The data of Example 15 suggest that antibody solution #1 measures mainly free troponin I, solution #2 measures both free troponin I and troponin I bound in the ternary complex and solution #3 measures mainly troponin I bound in the ternary complex. Thus, the conclusions from Example 15 taken together with the data in Table 8, indicate that substantial amounts of both free and bound troponin I are present in the diluted plasma sample. Among the three antibody solutions used in the immunoassays, solution #2 gives the largest assayed troponin I concentration, as expected, because the immunoassay using antibody solution #2 measures both free and bound troponin I. Thus, antibody solution #2 appears to provide the most comprehensive measure of troponin I in the plasma sample. Antibody solution #2 standardized with the purified troponin complex gave the most stable assay with respect to inhibitor addition and assay incubation time. The decrease of troponin I concentration at 2.5 h measured with antibody solution #2 standardized with free Troponin I is due to an increase at 2.5 h of the slope of the standard curve.

TABLE 8

| Antibody solution | Time after antibodies added, (hours) | Standard used to determine troponin I concentration | Troponin I concentration in plasma, (ng/ml) | | Ratio |
|---|---|---|---|---|---|
| | | | Without binding inhibitors | With binding inhibitors | |
| #1 | 0.5 | Troponin I | 91 | 186 | 2.0 |
| #1 | 2.5 | Troponin I | 83 | 251 | 3.0 |
| #3 | 0.5 | Ternary Troponin Complex | 134 | 108 | 0.8 |
| #3 | 2.5 | Ternary Troponin Complex | 87 | 65 | 0.74 |
| #2 | 0.5 | Troponin I | 280 | 360 | 1.3 |
| #2 | 2.5 | Troponin I | 172 | 220 | 1.3 |
| #2 | 0.5 | Ternary Troponin Complex | 229 | 299 | 1.3 |
| #2 | 2.5 | Ternary Troponin Complex | 223 | 286 | 1.3 |

Example 17

Immunoassay of Free Human Cardiac Troponin T and Troponin T in the Human Cardiac Ternary Complex Two antibody stock solutions (#1 and 2) were prepared as described below in metal-free assay buffer either with or without binding inhibitors (30 mM EDTA and 0.15 mM Melittin) and with the following antibodies:

1. 30 μg/ml 1A12 anti troponin I, 30 μg/ml 9B1 anti troponin T and 7.5 μg/ml biotinylated anti troponin T peptide 3 specific (Biospacific).
2. 30 μg/ml 9B1 anti troponin T and 7.5 μg/ml biotinylated anti troponin T peptide 3 specific.

Human-cardiac troponin ternary complex (Bio-tech International, Inc.) was diluted to 1–20 ng/ml troponin T in metal free assay buffer and purified Human cardiac troponin T (Scripps Labs) was diluted to 1.5, 3.0 and 6.0 ng/ml in the same buffer. The dilutions of the troponin complex and troponin T were assayed immediately using Protocol B, Example 2 with antibody solutions #1 and #2. Aliquots of the reaction mixtures formed by the addition of the antibodies to the troponin complex and troponin T samples were taken at 0.5 h and 3.0 h after the antibodies were added and were further treated as described in Example 2, Protocol B. The results are shown in Table 9 and are expressed in terms of an assay slope with units of $OD_{490}$ per ng/ml total troponin T in the linear range of the assay. A higher slope indicates better binding of the antibodies to the troponin components.

The data show that the antibodies in solution #1 recognize both free troponin T and troponin T bound in the ternary complex equally well. The antibodies in solution #2 recognize free troponin T well but recognizes troponin T in the ternary complex poorly. Thus, antibody solution #1 is expected to provide the most comprehensive and accurate measure of the total concentration of troponin T in human blood samples in which a substantial amount of the ternary complex is present.

TABLE 9

| Antibody solution | Time after antibodies added to troponin sample (hours) | Assay slope (OD490 per ng/ml troponin T) | | | |
|---|---|---|---|---|---|
| | | Free troponin T without binding inhibitors | Free troponin T with binding inhibitors | Troponin complex without binding inhibitors | Troponin complex with binding inhibitor |
| #1 | 0.5 | 0.069 | 0.078 | 0.061 | 0.070 |
| #2 | 0.5 | 0.078 | 0.085 | 0.013 | 0.012 |
| #2 | 3.0 | >0.08 | >0.08 | 0.018 | 0.023 |

Example 18

Use of Troponin C to Prevent Non-specific Binding of Troponin I to Filter Membranes Oxidized cardiac troponin I (air oxidized, Example 4, University of Birmingham) at 100 ng/ml final concentration in human serum (Hybritech, Inc., San Diego) was incubated either with or without 100 ug/ml human cardiac troponin C (Bio-tech International, Inc.) at room temperature for 30 minutes. Two filter membranes, a CytoSep filter (Ahlstrom Filtration, Mount Holly Springs, Pa.) and a glass fiber filter (GB-100R, Micro Filtration Systems, Dublin, Calif.) were cut into rectangles measuring 1.5 cm by 3.0 cm and were secured to a transparency film (catalog #pp2500, 3M, Austin, Tex.) by a piece of tape across the filters. The troponin I solutions with and without troponin C (300 μl) were applied slowly to the top of the filters at one end and the solution migrated through the filter to the far end by wicking action. About 15 μl of solution was collected from the far end with a plastic pipet tip. The collected solutions were diluted by factors of 20, 40 and 80 in assay buffer and assayed using Protocol A, Example 2 with TRI-7 F81 anti troponin I conjugate and biotinylated anti troponin I peptide 3 specific antibodies. Aliquots of the troponin I solutions with and without troponin C that had not been passed through the filters were also assayed and used to construct a standard curve from which the concentration of troponin I in the solution that had passed through the membrane was determined. The calculated concentration was divided by 100 ng/ml to obtain the fraction of recovered troponin I shown in Table 10. The experimental errors given in Table 10 represent one standard deviation.

The data show that the presence of troponin C helps to lower the non-specific binding of troponin I to the filter membranes.

TABLE 10

| | Fraction of troponin I recovered | |
|---|---|---|
| Filter | Without troponin C | With troponin C |
| CytoSep | 0.03 ± 0.03 | 0.15 ± 0.04 |
| Glass Fiber | 0.00 ± 0.03 | 0.09 ± 0.04 |

Example 19

Use of Proteins of High Isoelectric Point to Prevent Non-specific Binding of Troponin I to Filter Membranes A blood filter (CytoSep 1.5 cm×3.0 cm) was soaked for 16 hours at room temperature in solutions of deionized water containing 1 mg/ml of the proteins listed in Table 11. The filters were rinsed once with deionized water and dried for 2 hours at 35 C. Oxidized human cardiac troponin I (Biotech International, Inc.) at 100 ng/ml in human serum (Hybritech, Inc., San Diego, Calif.) also containing 2 mM added calcium chloride was passed through the filters as described in Example 18. The amount of troponin I recovered from the filters was determined by assay (Protocol B, Example 2) using TRI-7 F81 anti-troponin I and biotinylated anti troponin I peptide 4 specific antibodies with added binding inhibitors (Example 11). The data in Table 11 are expressed as the fraction of troponin I recovered, which was determined as described in Example 18.

The results show that Melittin and protamine sulfate substantially reduces the non-specific binding of troponin I to the blood filter, whereas casein and non-fat dried milk had little effect at the concentrations tested.

TABLE 11

| Protein | Fraction of troponin I recovered |
|---|---|
| No addition | 0.16 |
| Protamine Sulfate | 0.77 |
| Casein | 0.16 |
| Melittin | 0.72 |
| Non-fat dried milk | 0.08 |

Example 20

Immunoassay of Ternary Troponin Complex using TRI-7 F81 anti Troponin I and Biotinylated anti Troponin I Peptide 4 Antibodies The purified ternary troponin complex (Bio-tech International, Inc.) was assayed for troponin I as described in Example 13, except that the title antibody pair was used in the immunoassay and the aliquot of the reaction mixture of the antibodies with the troponin sample was taken three hours after the antibodies were added to the troponin. The fractional assay response was 0.16 in the absence of binding inhibitors and 0.49 in the presence of binding inhibitors.

The data show that the title antibody pair recognizes troponin I in the ternary complex poorly. In example 10, it was shown that the presence of troponin C without Troponin T had little effect on the recognition of the title antibody pair for troponin I. Thus, the title antibody pair can bind to troponin I present in the binary complex with troponin C better than it can bind to Troponin I present in the ternary complex.

Example 21

Immunoassay of Troponin I in Plasma from a Patient with Confirmed Myocardial Infarction using TRI-7 F81 Anti Troponin I Conjugate and Biotinylated Anti Troponin I Peptide 1 Specific Antibodies Frozen plasma from a patient with a confirmed myocardial infarction was thawed and diluted in human serum (Hybritech Inc., San Diego, Calif.) also containing 0.5 M added sodium chloride and assayed for troponin I with the title antibody pair using Protocol A, Example 2. Oxidized purified human cardiac troponin I (University of Birmingham) was assayed and used to construct a standard curve from which the troponin I in the plasma was determined. The neat plasma sample was refrozen in a −70 C freezer after being on ice for several hours. The frozen plasma was rethawed at room temperature and was assayed using the same protocol as described above except the plasma and troponin I standards were diluted into assay buffer. The standards exhibited almost identical assay slopes when diluted in serum (first assay) or assay buffer (second assay). The neat plasma sample was further incubated at 4 C for the times indicated in Table 12 and reassayed in assay buffer.

The data show a substantial increase in the assayed troponin I concentration after a freeze/thaw cycle and after incubation at 4 C. This assay instability may be associated with the opening up or partial unraveling of the ternary troponin complex by the freeze/thaw cycle.

TABLE 12

| Time of assay | Assayed concentration of troponin I |
|---|---|
| After first thaw of plasma | 284 ng/ml |
| 2 hours after second thaw of plasma | >800 ng/ml |
| 19 hours after second thaw of plasma | 1760 ng/ml |
| 90 hours after second thaw of plasma | 2300 ng/ml |

Example 22

Expression, Screening and Selection of Recombinant Antibodies (Binding Fragments or Fab Fragments)

Immunization of Mice

Mice were immunized by the following method. Each of ten mice were immunized intraperitoneally using 50 μg protein antigen (troponin I and troponin ternary complex) emulsified in Freund's complete adjuvant on day 0, and day 28. Test bleeds of mice were obtained through puncture of the retro-orbital sinus. When the titers were determined to be high for biotinylated antigen, the mice were boosted with 50 μg of protein on day 70, 71, and 72, with subsequent sacrifice and splenectomy on day 77. If titers of antibody were not satisfactory, mice were boosted with 50 μg antigen on day 56 and a test bleed was obtained on day 63. If satisfactory titers were obtained the animals were boosted with 50 μg of antigen on day 98, 99, and 100 and the spleens extracted on day 105.

Antibody Phage Display Libraries

Mice having high titers of antibodies to the desired protein antigen (troponin I or troponin ternary complex) were sacrificed, and total RNA was purified from the spleen cells (Anal. Biochem. 162:156–159 (1987)). The total RNA (50 μg) from the spleen cells was used directly as template for Superscript™ II reverse transcriptase (Gibco BRL, Gaithersburg, Md.) with oligo $(dT)_{12}$ as the primer to make cDNA for PCR. A total of 32 PCR reactions was used to amplify the heavy chain variable regions using Taq DNA polymerase (Boehringer Mannheim, Indianapolis, Ind.), 3 μL cDNA per reaction, 32 different 5' oligonucleotides and a single 3' oligonucleotide. The kappa chain variable regions were amplified similarly using 29 different 5' oligonucleotides and a single 3' oligonucleotide. The oligonucleotides were previously designed to ensure that nearly all antibody variable regions present in the spleen would be amplified with no more than 2 changes in the actual amino acid sequence caused by mismatches of the oligonucleotide with the cDNA based on a compilation of mouse antibody sequences. (Sequences of proteins of immunological interest. Vol. 2., 5th edition, 1991, Cambridge, Mass.) An aliquot of each double stranded PCR product was amplified a second time using only the 3' oligonucleotide to produce single stranded DNA (ss-DNA). The ss-DNA products from all of the kappa chain amplification reactions were pooled, and the ss-DNA products from all of the heavy chain reactions were pooled separately. The ss-DNA from each pooled sample was purified using high performance liquid chromatography (HPLC) and a Genpak Fax HPLC column (Waters Inc, Milford, Mass.). The purified ss-DNA was used to perform mutagenesis of an M13 uracil template following standard oligonucleotide directed mutagenesis techniques (J. Immunol. 149:3903–3913, 1992). The M13 template contains DNA sequences complementary to the 5' and 3' ends of the ss-DNA for both the heavy chain and the kappa chain variable regions. As a result, when the heavy chain and kappa chain variable regions were annealed to the M13 vector, a mixture of different antibody sequences was created. The resulting antibodies were expressed as Fab antibody fragments comprising the entire kappa chain and the variable region of the heavy chain linked to the first constant region of the heavy chain. Electrocompetent cells (DH12S Gibco BRL., Gaithersburg, Md.) were transformed by electroporation with the resultant M13 DNA. A typical electroporation of 500 ng M13 vector into 40/L DH12S cells yielded $10^7$ to $10^8$ different antibody clones. The clones were further amplified to produce an antibody phage display library. The M13 vector was designed so that the heavy chain was expressed as a fusion protein with the major coat protein of M13, the gene VIII protein. There are approximately 2700 copies of the gene VIII protein on every phage particle. After the heavy chain/gene VIII fusion protein was secreted to the periplasm of E. coli, the secreted kappa chain binds to the heavy chain to form a functional antibody Fab fragment. This leads to the production of phage having functional antibodies on the surface of the phage with the DNA encoding the antibody packaged inside the phage.

Screening of Antibody Phage Display Libraries

The antibody phage display library obtained from electroporating the M13 mutagenesis DNA into E. coli consists of many different antibodies displayed on phage particles (antibody phage). The number of high affinity antibodies to the protein antigen is low. The following screening procedure was developed to isolate antibodies specific to troponin I and the troponin ternary complex. Antibody phage was incubated with biotinylated, oxidized troponin I ($10^{-9}$M, 10 biotins/protein) or biotinylated troponin ternary complex ($10^{-9}$M, 11 biotins/protein) in solution to equilibrium. The antibody phage binding to biotinylated protein antigen was isolated by incubation with magnetic latex coated with avidin. The nonspecific antibody phage were washed away, and antibody phage binding to latex was eluted and amplified by growth in XL1 blue E. coli cells (Stratagene, La Jolla, Calif.). The amplified antibody phage were then subjected to a second round of selection. Since the incubation of biotinylated protein antigen and antibody phage was performed in solution, the concentration of biotinylated protein antigen was adjusted to select only for high affinity antibodies. The process described above was repeated until the antibody phage consisted of a high percentage of phage encoding troponin antibodies. The antibody sequences were then ready for subcloning.

Antibody Subcloning

The entire antibody DNA sequence was amplified using a 5' oligonucleotide binding to the signal sequence of the kappa chain, which is on the 5' side of the heavy chain, and a 3' oligonucleotide binding to the end of the heavy chain constant region sequence. After amplification, the DNA was purified using agarose gel electrophoresis, then annealed and ligated to a pBR322 expression vector. Transformation of DH10B cells by electroporation was accomplished using this DNA, and the cells were grown on tetracycline plates to select clones containing the inserted DNA. Colonies were transferred into 3 mL 2YT media with 10 µg/mL tetracycline, and cultures were grown overnight at $37_fC$. Overnight cultures of cells were diluted 1:100 into 50 mL 2YT media with 1% glycerol and 10 mg/mL tetracycline in 250 mL baffled shake flasks to obtain sufficient antibody for testing. Cultures were grown at $37_fC$ until the absorbance of the culture at 600 nm was between 2 and 4. At that point, cultures were induced and grown overnight at $23_fC$. The cells were disrupted in a high pressure homogenizer, and the antibody was purified.

Antibody Characterization by Epitope Mapping

The antibodies produced were characterized with regard to their ability to perform in a double antibody, solid-phase, noncompetitive enzyme immunoassay (sandwich assay). Antibody Fab fragments (Fab) were selected to bind distinctly different epitopes on the protein antigen so that the binding of one Fab did not sterically hinder the binding of the second Fab. The protein antigen was labeled with biotin by using biotin-XX-NHS ester (Molecular Probes, Portland, Oreg.). The biotinylation of the protein antigen was sufficiently low in molar ratio of biotin to protein (on average, 4 biotin/protein) so that the probability of an epitope being substantially affected with regard to the native structure of the antibody binding site was minimal. The first Fab fragment was incubated in microtiter plate wells which contained adsorbed, affinity-purified goat-anti-mouse Fab. The wells were washed and a blocking solution containing a non-specific mouse Fab at high concentrations was placed in each well to saturate remaining anti-Fab sites. In separate microtiter plate wells, the second Fab fragment was incubated to equilibrium with the biotinylated protein antigen. The second Fab was present in substantial molar excess over the biotinylated protein antigen. The mixture containing the second Fab and the biotinylated protein was added to the microtiter plate wells that were coated with the first Fab and incubated. A conjugate of streptavidin and alkaline phosphatase was added to the mixture to bind to the biotinylated protein to detect the presence of the protein antigen. The microtiter wells were washed and the presence of bound alkaline phosphatase was detected by adding phenolphthalein monophosphate, and the rate of product formation at 560 nm was determined using a spectrophotometric microtiter plate reader. The excess non-specific mouse Fab in the mixture prevented the second Fab from binding to anti-Fab adsorbed to the wells of the microtiter plate. Controls were performed using the same Fab as the first and second Fab to show that when the epitope bound by the second Fab is the same as the first, very little binding of the alkaline phosphatase to the microtiter plate well was observed. If the two different Fab fragments being tested can bind to different epitopes on the same protein, then the amount of alkaline phosphatase activity bound to the well was substantially greater than that of the control. The advantage of this assay procedure is that the antibodies were unlabeled so that many antibodies can be rapidly assayed to determine if they bind distinctly different epitopes. The number of distinct epitopes was determined and antibodies were grouped according to their epitope specificity.

Example 23

Characterization and Selection of Complementary Antibody Pairs for Recognition of Oxidized and Reduced Free Troponin I and Troponin I Bound in the Ternary Complex Antibodies directed to troponin I were tested in a sandwich immunoassay in pairs consisting of an antibody conjugate antibody and a complementary biotinylated antibody (example 1). The antibodies tested were anti troponin I recombinant antibodies that were originally raised to free troponin I but were selected to bind both free troponin I and troponin I in the ternary complex (example 22). Goat anti troponin I peptide 3 specific polyclonal antibody was also tested.

Purified human cardiac ternary troponin complex (Bio-Tech International) was diluted into assay buffer and assayed (protocol A, Example 2) with the complementary antibody pairs shown in Table 13. The results are expressed as an assay slope with units of $OD_{490}$ per ng/ml total troponin I in the linear range of the assay. A higher slope indicates better binding of the antibodies to the troponin I.

Troponin I was prepared by dissociating the components of the ternary troponin complex under oxidizing (hereafter called dissociated/oxidized sample) and reducing (hereafter called dissociated/reduced sample) conditions. Purified human cardiac ternary troponin complex was incubated at 4 ug/ml for 4 hours at room temperature in a dissociation buffer consisting of 50 mM 3-(N-morpholino) propane sulfonic acid, 150 mM sodium chloride, 6 M urea, 10 mM EDTA and 0.05 mM Melittin, pH 7.0, to form the dissociated/oxidized sample. The dissociated/oxidized sample was diluted to 1–30 ng/ml (total protein concentration) in assay buffer and assayed (protocol A, Example 2) with the complementary antibody pairs shown in Table 13. The same procedure was used to form and assay the dissociated/reduced sample except that the dissociation and assay buffers contained also 1.5 mM DTT to reduce the intramolecular disulfide of troponin I.

To show that the dissociation procedure did not harm free troponin I with respect to assays of free troponin I, purified oxidized troponin I (Bio-Tech International) was treated using the procedure to form the dissociated/oxidized sample and was then assayed with ten different complementary antibody pairs (pairs 19–28 in Table 13). The assay results (not shown) were compared with those obtained on purified oxidized troponin I that was not treated with the dissociation procedure. No significant difference between the assay results for the treated and the untreated purified troponin I was observed for any of the ten tested antibody pairs.

The antibody pair (#29, Table 13) consisting of biotinylated 9B1 anti troponin T monoclonal and Goat anti troponin I peptide 3 specific polyclonal conjugate antibodies does not recognize troponin I that is dissociated from the ternary complex (Example 15), which is consistent with the zero assay slope obtained for this antibody pair with the dissociated/oxidized and dissociated/reduced samples.

The data (Table 13) show that antibodies directed to troponin I can be generated and selected to form an immunoassay that gives essentially the same assay response (slope) for troponin I in the ternary complex, the dissociated/oxidized and the dissociated/reduced samples (for example, antibody pair #17). Thus, an antibody pair such as #17 could be used to measure the total concentration of troponin I in a sample containing all of the forms of troponin I that were tested. The procedure used to generate and select the antibodies produces antibodies that are good candidates for use in an assay that measures oxidized and reduced free troponin I and troponin I in the ternary complex in the blood of patients who have suffered a myocardial infarction.

TABLE 13

| | | | Assay Slope ($OD_{490}$ per ng/ml troponin I) | | |
|---|---|---|---|---|---|
| Pair # | Conjugate Antibody | Biotinylated Antibody | Ternary Complex | Dissociated (oxidized) | Dissociated (reduced) |
| 1 | Goat anti troponin I Peptide 3 Specific | Recombinant anti troponin I #4 | 0.78 | 0.72 | 1.23 |
| 2 | Goat anti troponin I Peptide 3 Specific | Recombinant anti troponin I #16 | 0.77 | 0.55 | 0.53 |
| 3 | Goat anti troponin I Peptide 3 Specific | Recombinant anti troponin I #19/33 | 1.07 | 0.77 | 0.77 |
| 4 | Goat anti troponin I Peptide 3 Specific | Recombinant anti troponin I #28/36 | 0.58 | 0.67 | 1.03 |
| 5 | Goat anti troponin I Peptide 3 Specific | Recombinant anti troponin I #49 | 0.73 | 0.51 | 0.52 |
| 6 | Goat anti troponin I Peptide 3 Specific | Recombinant anti troponin I #50 | 0.70 | 0.61 | 0.98 |
| 7 | Goat anti troponin I Peptide 3 Specific | Recombinant anti troponin I #51 | 0.89 | 0.66 | 0.69 |
| 8 | Goat anti troponin I Peptide 3 Specific | Recombinant anti troponin I #53 | 0.55 | 0.86 | 0.89 |
| 9 | Goat anti troponin I Peptide 3 Specific | Recombinant anti troponin I #26 | 0.21 | 0.12 | 0.18 |
| 10 | Goat anti troponin I Peptide 3 Specific | Recombinant anti troponin I #27 | 0.54 | 0.38 | 0.46 |
| 11 | Goat anti troponin I Peptide 3 Specific | Recombinant anti troponin I #29 | 0.78 | 0.58 | 0.60 |
| 12 | Goat anti troponin I Peptide 3 Specific | Recombinant anti troponin I #31 | 0.60 | 0.52 | 0.64 |
| 13 | Goat anti troponin I Peptide 3 Specific | Recombinant anti troponin I #32 | 0.78 | 0.64 | 0.58 |
| 14 | Goat anti troponin I Peptide 3 Specific | Recombinant anti troponin I #54 | 0.23 | 0.54 | 0.45 |
| 15 | Goat anti troponin I Peptide 3 Specific | Recombinant anti troponin I #55 | 0.23 | 0.52 | 0.47 |
| 16 | Goat anti troponin I Peptide 3 Specific | Recombinant anti troponin I #56 | 0.69 | 0.99 | 1.05 |
| 17 | Goat anti troponin I | Recombinant anti | 1.02 | 1.08 | 1.08 |

TABLE 13-continued

| | | | Assay Slope ($OD_{490}$ per ng/ml troponin I) | |
|---|---|---|---|---|
| Pair # | Conjugate Antibody | Biotinylated Antibody | Ternary Complex | Dissociated (oxidized) | Dissociated (reduced) |
| 18 | Goat anti troponin I Peptide 3 Specific | Recombinant anti troponin I #58 | 0.39 | 0.90 | 0.95 |
| 19 | Recombinant anti troponin I #49 | Recombinant anti troponin I #4 | 0.48 | 0.52 | 1.06 |
| 20 | Recombinant anti troponin I #49 | Recombinant anti troponin I #28/36 | 0.21 | 0.41 | 0.96 |
| 21 | Recombinant anti troponin I #49 | Goat anti Troponin I Peptide 3 Specific | 1.18 | 1.12 | 1.25 |
| 22 | Recombinant anti troponin I #51 | Recombinant anti troponin I #4 | 2.42 | 3.31 | 7.63 |
| 23 | Recombinant anti troponin I #51 | Recombinant anti troponin I #28/36 | 1.20 | 2.52 | 5.69 |
| 24 | Recombinant anti troponin I #50 | Recombinant anti troponin I #16 | 1.33 | 0.53 | 1.20 |
| 25 | Recombinant anti troponin I #50 | Recombinant anti troponin I #19/33 | 1.93 | 0.81 | 1.95 |
| 26 | Recombinant anti troponin I #50 | Goat anti Troponin I Peptide 3 Specific | 1.92 | 1.52 | 2.12 |
| 27 | Recombinant anti troponin I #53 | Recombinant anti troponin I #16 | 1.58 | 3.33 | 3.49 |
| 28 | Recombinant anti troponin I #53 | Recombinant anti troponin I #33/79 | 1.60 | 3.75 | 4.28 |
| 29 | Goat anti Troponin I Peptide 3 Specific | 9B1 anti troponin T monoclonal | 0.47 | 0.00 | 0.00 |

Example 24

Effect of Protamine and Melittin on the Non-Specific Absorption of Troponin to Latex Particles Avidin-HS coated magnetic latex (Example 1) was washed and resuspended to 1% solids in three different diluents: serum (Hybritech Inc., San Diego, Calif.), serum containing 0.2 mg/ml protamine chloride and serum containing 0.1 mM melittin. A 125 µl volume of each resuspended latex solution was mixed with a 125 µl volume of serum containing either 6 ng/ml of oxidized purified troponin I (Bio-Tech International, Inc) or 18 ng/ml of purified ternary troponin complex to form a solution of troponin and latex. Also, a 125 µl volume of serum, serum containing 0.2 mg/ml protamine chloride or serum containing 0.1 mM Melittin was mixed with a 125 ul volume of serum containing either 0.6 ng/ml of oxidized purified troponin 1 or 18 ng/ml of purified ternary complex to form a solution of troponin without latex. The solutions were incubated for 30 minutes at room temperature. The latex was pelleted and the supernatants collected. The supernatants from the solutions of troponin and latex and the solutions of troponin without latex were assayed for troponin (Protocol A, Example 2, except serum was used in place of assay buffer) using antibody pair #17 (Table 13) to determine the concentration of troponin. For each diluent, the fraction of troponin recovered in the supernatants of the solutions of troponin and latex (Table 14) was determined by dividing the measured concentration of troponin in the supernatant from the solution of troponin and latex by the measured concentration of troponin in the solution of troponin without latex.

The data show that both melittin and protamine chloride increase the recovery of troponin, indicating that melittin and protamine chloride reduce the non-specific absorption of troponin to the latex.

TABLE 14

| | Fraction of Troponin Recovered in the Supernatant | | |
|---|---|---|---|
| Troponin Form | No Addition | + Protamine Chloride | + Melittin |
| Free Oxidized Troponin I | 0.49 | 0.73 | 0.80 |
| Troponin Complex | 0.58 | 0.87 | 0.77 |

Example 25

Effect of Protamine and Melittin on the Assay Response of a Sandwich Immunoassay for Troponin that Utilizes Latex Particles Avidin-HS magnetic latex (Example 1) was washed and resuspended to 1% solids in two different diluents: assay buffer and assay buffer containing 0.1 mM melittin. In the wells of a microtiter plate, 25 µl of each resuspended latex solution was mixed with 25 µl of assay buffer containing purified oxidized troponin I (Bio-Tech International) at various concentrations between 0 and 16 ng/ml to form a solution of troponin I and latex. The solutions were incubated at room temperature for 30 minutes. To each well was added 50 µl of a solution consisting of the two antibodies of pair #17 (Table 13), each at 2.5 µg/ml, to form a reaction mixture. The reaction mixture was incubated for 15 minutes and the latex was then pelleted, washed and further treated as described in Protocol A (Example 2). The results are expressed in Table 15 as an assay slope with units of $OD_{490}$ per ng/ml troponin I.

The data show that the addition of melittin to the assay increases the assay response by about a factor of two, thus increasing assay sensitivity to troponin I. In data not shown, incorporation of protamine (at 0.03–0.1 mg/ml) and melittin (at 0.017–0.05 mM) into an immunoassay for troponin I that utilized latex particles increased the assay response by factors of 30% to 400%.

TABLE 15

| Additive | Assay Slope |
|---|---|
| None | 0.021 |
| Melittin | 0.040 |

We claim:

1. An antibody or a fragment thereof, immobilized on a solid phase, that specifically binds cardiac troponin I, wherein said antibody is insensitive with respect to each form of cardiac troponin I selected from the group consisting of free cardiac troponin I, cardiac troponin I in a binary complex with troponin C, and cardiac troponin I in a ternary complex with troponin C and troponin T.

2. An antibody, or fragment thereof, conjugated to a signal generating element, that specifically binds cardiac troponin I, wherein said antibody is insensitive with respect to each form of cardiac troponin I selected from the group consisting of free cardiac troponin I, cardiac troponin I in a binary complex with troponin C, and cardiac troponin I in a ternary complex with troponin C and troponin T.

3. A method of selecting antibodies for an immunoassay for cardiac troponin I, the method comprising:
   selecting two or more antibodies that, when used in said immunoassay, provide an assay response that is insensitive with respect to each form of cardiac troponin I selected from the group consisting of free cardiac troponin I, cardiac troponin I in a binary compled with troponin C, and cardiac troponin I in a ternary complex with troponin C and troponin T.

4. A method according to claim 3, wherein said two or more antibodies are independently selected from the group consisting of monoclonal antibodies, recombinant antibodies and polyclonal antibodies.

5. A method according to claim 3, wherein said at least two antibodies are selected to provide a signal that is within about 20% for equimolar amounts of each said form of cardiac troponin I.

6. A method according to claim 3, wherein said method comprises selecting two antibodies, each of which is insensitive with respect to each form of cardiac troponin I selected from the group consisting of free cardiac troponin I, cardiac troponin I in a binary complex with troponin C, and cardiac troponin I in a ternary complex with troponin C and T.

7. A composition comprising:
   one or more antibodies, or fragments thereof, immobilized on a solid phase, wherein each form of cardiac troponin I selected from the group consisting of free cardiac troponin I, cardiac troponin I in a binary complex with troponin C, and cardiac troponin I in a ternary complex with troponin C and troponin T binds to one or more of said antibodies.

8. A composition comprising:
   one or more antibodies, or fragments thereof, conjugated to a signal generating element, wherein each form of cardiac troponin I selected from the group consisting of free cardiac troponin I, cardiac troponin I in a binary complex with troponin C, and cardiac troponin I in a ternary complex with troponin C and troponin T binds to one or more of said antibodies.

9. The composition of claim 7 or 8, wherein said antibodies are selected from the group consisting of monoclonal antibody, recombinant antibody and polyclonal antibody.

10. The composition of claim 7 or 8, wherein said antibodies are a pool of two or more antibodies.

11. The composition of claim 7 or 8, wherein said antibodies are unable to distinguish between said forms of cardiac troponin I.

12. A method of selecting antibodies to cardiac troponin I, said method comprising:
    selecting one or more antibodies, wherein each form of cardiac troponin I selected from the group consisting of free cardiac troponin I, cardiac troponin I in a binary complex with troponin C, and cardiac troponin I in a ternary complex with troponin C and troponin T binds to one or more of said antibodies.

13. The method of claim 12, wherein said antibodies are selected from the group consisting of monoclonal antibody, recombinant antibody and polyclonal antibody.

14. The method of claim 12, wherein said antibodies are a pool of two or more antibodies.

15. The method of claim 12, wherein said antibodies are unable to distinguish between said forms of cardiac troponin I.

16. A composition comprising:
    one or more first antibodies, or fragments thereof, immobilized on a solid phase, wherein each form of cardiac troponin I selected from the group consisting of free cardiac troponin I, cardiac troponin I in a binary complex with troponin C, and cardiac troponin I in a ternary complex with troponin C and troponin T binds to one or more of said first antibodies; and
    one or more second antibodies, or fragments thereof, conjugated to a signal generating element, wherein each form of cardiac troponin I selected from the group consisting of free cardiac troponin I, cardiac troponin I in a binary complex with troponin C, and cardiac troponin I in a ternary complex with troponin C and troponin T binds to one or more of said second antibodies.

17. The composition of claim 16, wherein said first and second antibodies are independently selected from the group consisting of monoclonal antibody, recombinant antibody and polyclonal antibody.

18. The composition of claim 16, wherein said first and second antibodies are a pool of two or more antibodies.

19. A method of selecting antibodies for a sandwich immunoassay, the method comprising:
    selecting one or more first antibodies and one or more second antibodies, wherein each form of cardiac troponin I selected from the group consisting of free cardiac troponin I, cardiac troponin I in a binary complex with troponin C, and cardiac troponin I in a ternary complex with troponin C and troponin T binds to one or more of said first and second antibodies.

20. The method of claim 19 wherein said first and second antibodies are independently selected from the group consisting of monoclonal antibody, recombinant antibody and polyclonal antibody.

21. The method of claim 19, wherein said first and second antibodies are a pool of two or more antibodies.

* * * * *